(12) United States Patent
Hurley et al.

(10) Patent No.: US 9,468,542 B2
(45) Date of Patent: Oct. 18, 2016

(54) PROSTHETIC SOCKET AND SOCKET LINER WITH MOISTURE MANAGEMENT CAPABILITY

(71) Applicant: LIM INNOVATIONS, INC., San Francisco, CA (US)

(72) Inventors: Garrett Ray Hurley, San Francisco, CA (US); Jesse Robert Williams, San Francisco, CA (US)

(73) Assignee: LIM Innovations, Inc., San Francisco, CA (US)

( * ) Notice: Subject to any disclaimer, the term of this patent is extended or adjusted under 35 U.S.C. 154(b) by 66 days.

(21) Appl. No.: 14/310,147

(22) Filed: Jun. 20, 2014

(65) Prior Publication Data

US 2014/0379097 A1 Dec. 25, 2014

Related U.S. Application Data

(60) Provisional application No. 61/837,778, filed on Jun. 21, 2013, provisional application No. 61/901,618, filed on Nov. 8, 2013.

(51) Int. Cl.
*A61F 2/78* (2006.01)
*A61F 2/80* (2006.01)

(52) U.S. Cl.
CPC .............. *A61F 2/80* (2013.01); *A61F 2/7812* (2013.01); *A61F 2002/7818* (2013.01); *A61F 2002/805* (2013.01); *A61F 2002/807* (2013.01)

(58) Field of Classification Search
CPC ..................... A61F 2/7812; A61F 2002/7818
See application file for complete search history.

(56) References Cited

U.S. PATENT DOCUMENTS

| | | | |
|---|---|---|---|
| 1,144,681 A | 6/1915 | Apgar |
| 1,893,853 A | 1/1933 | Tullis |
| 2,025,835 A | 12/1935 | Trautman |
| 2,229,728 A | 1/1941 | Eddels |
| 2,634,424 A | 4/1953 | O'Gorman |
| 2,759,271 A | 8/1956 | Von Duyke |

(Continued)

FOREIGN PATENT DOCUMENTS

| | | |
|---|---|---|
| DE | 319623 | 3/1920 |
| EP | 0204407 A2 | 12/1986 |

(Continued)

OTHER PUBLICATIONS

U.S. Appl. No. 61/794,949, filed Mar. 15, 2013.*
Alley, "The High-Fidelity Interface: Skeletal Stabilization through Alternating Soft Tissue Compression and Release", Myoelectric Symposium 2011, New Brunswick, Canada, Aug. 14-19, 2011. (3 pages).

(Continued)

*Primary Examiner* — David H Willse
(74) *Attorney, Agent, or Firm* — Dorsey & Whitney LLP; Scott M. Smith

(57) ABSTRACT

A moisture management liner device for a prosthetic socket may include an elongate, cup-shaped, elastomeric member and multiple fluid transport strips. The elastomeric member may include a first material and may extend from an open proximal end to a substantially closed distal end. The substantially closed distal end may include a fluid exit aperture to allow fluid to pass out of the liner device. The fluid transport strips may include a second material and may be disposed at spaced-apart intervals around a circumference of an internal surface of the elastomeric member, over at least a distal portion of the elastomeric member. The fluid transport strips may be configured to facilitate passage of fluid out of the liner device through the fluid exit aperture.

13 Claims, 15 Drawing Sheets

(56) References Cited

U.S. PATENT DOCUMENTS

| | | |
|---|---|---|
| 2,908,016 A | 10/1959 | Botko |
| 2,949,674 A | 8/1960 | Wexler |
| 3,678,587 A | 7/1972 | Madden |
| 4,161,042 A | 7/1979 | Cottingham et al. |
| 4,225,982 A | 10/1980 | Cochrane et al. |
| 4,300,245 A | 11/1981 | Saunders |
| 4,459,709 A | 7/1984 | Leal et al. |
| 4,704,129 A | 11/1987 | Massey |
| 4,715,124 A | 12/1987 | Harrington |
| 4,783,293 A | 11/1988 | Wellershaus et al. |
| 4,842,608 A | 6/1989 | Marx et al. |
| 4,872,879 A | 10/1989 | Shamp |
| 4,921,502 A | 5/1990 | Shamp |
| 4,988,360 A | 1/1991 | Shamp |
| 5,003,969 A | 4/1991 | Azer et al. |
| 5,014,441 A | 5/1991 | Pratt |
| 5,108,456 A | 4/1992 | Coonan, III |
| 5,116,382 A | 5/1992 | Steinkamp et al. |
| 5,133,777 A | 7/1992 | Arbogast et al. |
| 5,168,635 A | 12/1992 | Hoffman |
| 5,201,773 A | 4/1993 | Carideo, Jr. |
| 5,201,775 A | 4/1993 | Arbogast et al. |
| 5,246,464 A | 9/1993 | Sabolich |
| 5,312,669 A | 5/1994 | Bedard |
| 5,503,543 A | 4/1996 | Laghi |
| 5,520,529 A | 5/1996 | Heckel |
| 5,529,575 A | 6/1996 | Klotz |
| 5,529,576 A | 6/1996 | Lundt et al. |
| 5,651,792 A | 7/1997 | Telikicherla |
| 5,652,053 A | 7/1997 | Liegeois |
| 5,718,925 A | 2/1998 | Kristinsson et al. |
| 5,728,165 A | 3/1998 | Brown, Sr. |
| 5,800,565 A | 9/1998 | Biedermann |
| 5,824,111 A | 10/1998 | Schall et al. |
| 5,885,509 A | 3/1999 | Kristinsson |
| 5,888,215 A | 3/1999 | Roos et al. |
| 5,888,217 A | 3/1999 | Siemker |
| 6,033,440 A | 3/2000 | Schall et al. |
| 6,051,026 A | 4/2000 | Biedermann et al. |
| 6,206,932 B1 | 3/2001 | Johnson |
| 6,228,124 B1 | 5/2001 | Slemker et al. |
| 6,231,618 B1 | 5/2001 | Schall et al. |
| 6,368,357 B1 | 4/2002 | Schon et al. |
| 6,444,282 B1 | 9/2002 | Shirer |
| 6,458,163 B1 | 10/2002 | Slemker et al. |
| 6,497,028 B1 | 12/2002 | Rothschild et al. |
| 6,500,210 B1 | 12/2002 | Sabolich et al. |
| 6,576,022 B2 | 6/2003 | Meyer et al. |
| 6,669,736 B2 | 12/2003 | Slemker et al. |
| 6,700,563 B1 | 3/2004 | Koizumi |
| 6,761,743 B1 | 7/2004 | Johnson |
| 6,974,484 B2 | 12/2005 | Caspers |
| 7,090,700 B2 | 8/2006 | Curtis |
| 7,105,122 B2 | 9/2006 | Karason |
| 7,172,714 B2 | 2/2007 | Jacobson |
| 7,240,414 B2 | 7/2007 | Taylor, Sr. |
| 7,300,466 B1 | 11/2007 | Martin |
| 7,318,504 B2 | 1/2008 | Vitale et al. |
| 7,338,532 B2 | 3/2008 | Haberman et al. |
| 7,344,567 B2 | 3/2008 | Slemker |
| 7,402,265 B2 | 7/2008 | Jacobson |
| 7,479,163 B2 | 1/2009 | Slemker et al. |
| 7,591,857 B2 | 9/2009 | Slemker et al. |
| 7,658,720 B2 | 2/2010 | Johnson |
| 7,753,866 B2 | 7/2010 | Jackovitch |
| 7,762,973 B2 | 7/2010 | Einarsson et al. |
| 7,980,921 B2 | 7/2011 | Saravanos |
| 7,985,192 B2 | 7/2011 | Sheehan et al. |
| 8,083,807 B2 | 12/2011 | Auberger et al. |
| 8,088,320 B1 | 1/2012 | Bedard |
| 8,116,900 B2 | 2/2012 | Slemker et al. |
| 8,142,517 B2 | 3/2012 | Horie |
| 8,303,527 B2 | 11/2012 | Joseph |
| 8,323,353 B1 | 12/2012 | Alley et al. |
| 8,382,852 B2 | 2/2013 | Laghi |
| 8,403,993 B2 | 3/2013 | Aram et al. |
| 8,470,050 B2 | 6/2013 | Dillingham |
| 8,535,389 B2 | 9/2013 | McKinney |
| 8,576,250 B2 | 11/2013 | Sabiston et al. |
| 2002/0099450 A1 | 7/2002 | Dean et al. |
| 2003/0181990 A1 | 9/2003 | Phillips |
| 2004/0204771 A1 | 10/2004 | Swanson, Sr. |
| 2004/0260402 A1 | 12/2004 | Baldini et al. |
| 2006/0009860 A1 | 1/2006 | Price, Jr. |
| 2006/0020348 A1 | 1/2006 | Slemker et al. |
| 2007/0004993 A1 | 1/2007 | Coppens et al. |
| 2007/0078523 A1 | 4/2007 | Kholwadwala et al. |
| 2007/0152379 A1 | 7/2007 | Jacobson |
| 2007/0298075 A1 | 12/2007 | Borgia et al. |
| 2008/0269914 A1 | 10/2008 | Coppens et al. |
| 2009/0036999 A1 | 2/2009 | Egilsson et al. |
| 2009/0076625 A1 | 3/2009 | Groves et al. |
| 2009/0105844 A1 | 4/2009 | Ortiz |
| 2009/0240344 A1 | 9/2009 | Colvin et al. |
| 2009/0299490 A1 | 12/2009 | Summit |
| 2010/0036300 A1 | 2/2010 | Sheehan et al. |
| 2010/0036505 A1 | 2/2010 | Hassler |
| 2010/0082116 A1 | 4/2010 | Johnson et al. |
| 2010/0160722 A1 | 6/2010 | Kuyava et al. |
| 2010/0274364 A1 | 10/2010 | Pacanowsky et al. |
| 2011/0029096 A1 | 2/2011 | Laghi |
| 2011/0071647 A1 | 3/2011 | Mahon |
| 2011/0114635 A1 | 5/2011 | Sheehan |
| 2011/0160871 A1 | 6/2011 | Boone et al. |
| 2011/0232837 A9 | 9/2011 | Ottleben |
| 2011/0320010 A1 | 12/2011 | Vo |
| 2012/0022667 A1 | 1/2012 | Accinni et al. |
| 2012/0041567 A1 | 2/2012 | Cornell |
| 2012/0101417 A1 | 4/2012 | Joseph |
| 2012/0101597 A1 | 4/2012 | Bache |
| 2012/0143077 A1 | 6/2012 | Sanders et al. |
| 2012/0165956 A1 | 6/2012 | Li |
| 2012/0191218 A1 | 7/2012 | McCarthy |
| 2012/0215324 A1 | 8/2012 | King |
| 2012/0253475 A1 | 10/2012 | Kelley et al. |
| 2012/0271210 A1 | 10/2012 | Galea et al. |
| 2012/0271433 A1 | 10/2012 | Galea et al. |
| 2012/0293411 A1 | 11/2012 | Leithinger et al. |
| 2013/0123940 A1 | 5/2013 | Hurley et al. |
| 2013/0192071 A1 | 8/2013 | Esposito et al. |
| 2013/0197318 A1 | 8/2013 | Herr et al. |
| 2013/0245785 A1 | 9/2013 | Accini et al. |
| 2013/0282141 A1 | 10/2013 | Herr et al. |
| 2014/0005801 A1 | 1/2014 | Van der Watt et al. |
| 2014/0031953 A1 | 1/2014 | Mackenzie |
| 2014/0121783 A1 | 5/2014 | Alley |
| 2014/0149082 A1 | 5/2014 | Sanders et al. |
| 2014/0277585 A1* | 9/2014 | Kelley et al. ............ 623/36 |
| 2015/0168943 A1 | 6/2015 | Hurley et al. |

FOREIGN PATENT DOCUMENTS

| | | |
|---|---|---|
| EP | 1433447 A2 | 6/2004 |
| GB | 127451 A | 6/1919 |
| GB | 2080114 A | 2/1982 |
| WO | 91/16019 | 10/1991 |
| WO | 98/12994 | 4/1998 |
| WO | 00/03665 | 1/2000 |
| WO | 00/30572 | 6/2000 |
| WO | 2007/035875 | 3/2007 |
| WO | 2008/116025 | 9/2008 |
| WO | 2009/093020 | 7/2009 |
| WO | 2012/021823 | 2/2012 |
| WO | 2014/004709 | 1/2014 |
| WO | 2014/068269 A1 | 5/2014 |

OTHER PUBLICATIONS

Andrysek, "Lower-limb prosthetic technologies in the developing world: A review of literature from 1994-2010", Prosthetics and Orthotics International, Cardiff, Wales, UK; Dec. 2010; 34(4): pp. 378-398. (21 pages).

(56) References Cited

OTHER PUBLICATIONS

Conn, "Materials Science: A Look At Some of the Substances on the Market for Device Fabrication", O&P Almanac, Jun. 2012, pp. 28-31; downloaded from http://www.allardusa.com/pdf/articles/Materials%20Science%20Article%20-%20June%202012%20O%26P%20Almanac.pdf. (4 pages).
Fairley, M. "M.A.S. Socket: A Transfemoral Revolution", The O&P Edge, Jun. 2004; downloaded from www.oandp.com/articles/2004-06-03.asp. (4 pages).
Fairley, "From Academia to the Developing World: Student Engineers Create Collaborative Technologies", The O&P Edge Magazine, Oandp.com, (May 2011) pp. 1-3.
Filauer LLC and Centri, "COMFIL—Thermo Formable Composite Technique", Fillauer Fabrication Manuel, (Jun. 15, 2012) pp. 1-16.
Gard, S.A. "Overview of Lower Limb Prosthetics Research", WRAMC and the VA Orthopedic & Prosthetic Workshop, Arlington, VA, Nov. 17 and 18, 2003, pp. 1-48. (49 pages).
Geil, M.D. "Consistency, precision, and accuracy of optical and electromagnetic shape-capturing systems for digital measurement of residual-limb anthropometrics of persons with transtibial amputation", Journal of Rehabilitation Research and Development, vol. 44, No. 4 (2007); pp. 515-524, U.S.A. (10 pages).
Gerschutz, et al., "Mechanical Evaluation of Direct Manufactured Prosthetic Sockets", American Academy of Orthotists & Prosthetists, 38th Academy Annual Meeting and Scientific Symposium, U.S.A., Mar. 21-24, 2012; downloaded from http://www.oandp.org/publications/jop/2012/2012-19.pdf. (1 page).
Gleave, "A Plastic Socket and Stump Casting Technique for Above-Knee Prostheses", Orthopaedic and Prosthetic Appliance Department, Hong Kong Government Medical Department, The Journal of Bone and Joint Surgery, vol. 47B, No. 1, (Feb. 1965) pp. 1-3.
Greenwald, et al., "Volume Management: Smart Variable Geometry Socket (SVGS) Technology for Lower-Limb Prostheses", JPO Journal of Prosthetics and Orthotics, vol. 15, No. 3 (2003), pp. 107-112, U.S.A. (6 pages).
Hong, et al, "Dynamic Moisture Vapor Transfer through Textiles: Part I: Clothing Hygrometry and the Influence of Fiber Type", Textile Research Journal, Thousand Oaks, California, U.S.A., Dec. 1988; 58: 697-706, Abstract. (1 page).
Hwang, "Blooming Winner—Spark!", Spark Galleries, 2012/Spark/Concept, Spark Design Awards, (2012) p. 1.
Jana, "Designing a Cheaper, Simpler Prosthetic Arm", ZDNet, (Nov. 14, 2011) pp. 1-3.
Koike, et al., "The TC Double Socket Above-knee Prosthesis", Prosthetics and Orthotics International, vol. 5, Tokyo Metropolitan Rehabilitation Center for the Physically and Mentally Handicapped, (1981) pp. 129-134.
Krouskop, et al., "Computer-aided design of a prosthetic socket for an above-knee amputee", Journal of Rehabilitation Research and Development, vol. 24, No. 2 (Spring 1987) pp. 31-38, U.S.A. (8 pages).
Manucharian, "An Investigation of Comfort Level Trend Differences Between the Hands -On Patellar Tendon Bearing and Hands-Off Hydrocast Transtibial Prosthetic Sockets", JPO: Journal of Prosthetics and Orthotics, Washington, D.C., U.S.A.; vol. 23, No. 3, 2011: pp. 124-140. (17 pages).
Otto Bock Healthcare LLP, "Initial and Interim Prostheses", Otto Bock Healthcare LLP, Prosthetics Lower Extremities 2008, (Feb. 2013) pp. 1-8, www.ottobockus.com/cps/rde/xbcr/ob_us_en/08cat_1.pdf.
Otto Bock Healthcare LLP , "Ottobock: PU Resin Kit Polytol"; downloaded Dec. 17, 2012 from http://www.ottobock.com/cps/rde/xchg/ob_com_en/hs.xsl/17414.html. (2 pages).
Sanders, et al., "Residual limb volume change: Systematic review of measurement and management", Journal of Rehabilitation Research & Development, 2011, vol. 48: pp. 949-986, U.S.A. (29 pages).
Sathishkumar, et al., "A cost-effective, adjustable, femoral socket, temporary prosthesis for immediate rehabilitation of above-knee amputation", International Journal of Rehabilitation Research, Ljubljana, Slovenia, Mar. 2004, vol. 7, Issue 1; pp. 71-74, abstract. (1 page).
Smith, "Silver Linings for O&P Devices", The Academy Today, vol. 1, No. 4: Oct. 2005; downloaded from http://www.oandp.org/AcademyTODAY/2005Oct/7.asp. (4 pages).
Spaeth, JP , "Laser imaging and computer-aided design and computer-aided manufacture in prosthetics and orthotics", Physical Medicine and Rehabilitation Clinics of North America, Elsevier Publishing, Amsterdam, The Netherlands; Feb. 2006 17(1): 245-263, abstract. (2 pages).
Turner, "FIT for Everyone", Yanko Design—Form Beyond Junction, (Jul. 17, 2015) pp. 1-3.
Unknown Author "Hanger ComfortFlex Socket System for Prosthetic Devices:" website pages downloaded Nov. 28, 2012 from http://www.hanger.com/prosthetics/services/Technology/Pages/ComfortFlex.aspx. pp. 1-2.
Wilson Jr. "A Material for Direct Forming of Prosthetic Sockets", downloaded from http://www.oandplibrary.org/al/1970_01_053.asp; downloaded Dec. 14, 2012. (4 pages).
Wilson, "Recent Advances in Above-Knee Prosthetics", Artificial Limbs, vol. 12, No. 2, (1968), pp. 1-27.
Wu, et al, "CIR sand casting system for trans-tibial socket", Prosthet Orthol Int. Aug. 2003: 27(2): 146-52, abstract. (1 page).
Notification of the First Office Action issued by the State Intellectual Property Office of the People's Republic of China in connection with Chinese Application No. 2012-80066479.8, (May 26, 2015) pp. 1-9.
Extended Search Report issued by the European Patent Office for European Patent Application No. 12847452.5, (Jul. 21, 2015) pp. 1-7.
International Search Report issued by the US Patent Office for International Application No. PCT/US2012/064876, (Feb. 19, 2013) pp. 1-6.
Written Opinion issued by the US Patent Office for International Application No. PCT/US2012/064876, (Feb. 19, 2013) pp. 1-10.
International Search Report issued by the US Patent Office for International Application No. PCT/US2014/029773, (Jun. 13, 2014) pp. 1-4.
Written Opinion, for International issued by the US Patent Office for International Application No. PCT/US2014/029773, (Jun. 13, 2014) pp. 1-9.
International Search Report issued by the Australian Patent Office for International Application No. PCT/US2014/043500, (Aug. 14, 2014) pp. 1-13.
Written Opinion of the International Searching Authority issued by the Australian Patent Office for International Application No. PCT/US2014/043500, (Aug. 18, 2014) pp. 1-8.
International Search Report issued by the US Patent Office for International Application No. PCT/US15/021611, (Jun. 25, 2015) pp. 1-2.
International Search Report issued by the US Patent Office for International Application No. PCT/US2014/070666, (Mar. 31, 2015) pp. 1-2.
Written Opinion of the Searching Authority issued by the US Patent Office for International Application No. PCT/US2014/070666, (Mar. 31, 2015) pp. 1.
International Search Report, Australian Patent Office for PCT Application No. PCT/US2014/043500, Aug. 14, 2014, pp. 1-13.
Written Opinion of the International Searching Authority, Australian Patent Office for PCT Application No. PCT/US2014/043500, Aug. 14, 2014, pp. 1-8.
Compton, Compton table. "New plastics for forming directly on the patient." Prosthetics and Orthotics International, 1978, vol. 2, No. 1, pp. 43-47.
Fairley, Miki. Socket can be fabricated, modified, fitted-in one hour. O&P Edge Magazine. Jun. 2007.
Allard. Cut-4-Custom: Custom TLSO in less than an hour. O&P Edge Magazine. Jul. 2010.

(56) References Cited

OTHER PUBLICATIONS

Instamorph. Remoldable prosthetics. Apr. 2013. <www.instamorph.com/ideas/outdoors-and-ergonomics/remoldable-prosthetics>.
Burgess et al., "The Management of Lower Extremity Amputations: Surgery, Immediate Postsurgical Prosthetic Fitting, Patient Care," Prosthetic and Sensory Aids Service, Aug. 1969 (129 pages).
Author Unknown, "Pro-Active Dynamic Accommodating Socket," downloaded and printed Mar. 25, 2013 (4 pages).
International Search Report issued for International Patent Application No. PCT/US2014/043500, mailed Aug. 14, 2014 (13 pages).
Written Opinion issued for International Patent Application No. PCT/US2015/021611, mailed Jun. 25, 2015 (4 pages).

* cited by examiner

PROSTHETIC SOCKET AND SOCKET LINER WITH MOISTURE MANAGEMENT CAPABILITY

CROSS-REFERENCE TO RELATED APPLICATIONS

The present application claims priority to U.S. Provisional Patent Application No. 61/837,778 of Hurley and Williams, entitled "A Prosthetic Socket Liner With Moisture Management Features" and filed on Jun. 21, 2013, and to U.S. Provisional Patent Application No. 61/901,618 of Hurley and Williams, entitled "A Prosthetic Socket and Liner With Moisture Management Capability" and filed on Nov. 8, 2013.

INCORPORATION BY REFERENCE

All publications and patent applications mentioned in this specification are herein incorporated by reference to the same extent as if each such individual publication or patent application were specifically and individually indicated to be so incorporated by reference.

TECHNICAL FIELD

The embodiments described herein relate to medical devices and methods. More specifically, the embodiments relate to a moisture management system for use in a prosthetic socket.

BACKGROUND

Polymeric prosthetic socket liners are widely used as an interface between the surface of a residual limb and a prosthetic socket that grasps the residual limb and provides continuity of function between the residual limb and more distal prosthetic components. These socket liners provide padding or pressure distribution surfaces that create greater comfort for the patient, and they also participate in suspension of the prosthetic socket on the residual limb. Suspension usually relies both on the tenacity with which the liner maintains its grasp on the residual limb and on the tenacity with which the socket maintains its grasp on the liner. Satisfactory performance of the prosthesis as a whole depends on many factors, but the quality of the fit of the socket on the residual limb, an optimal liner solution, and the overall quality of suspension of the socket are all very important.

Polymeric prosthetic liners typically include materials such as silicone, urethane, and thermoplastic elastomer gels in the form of blends and block copolymers, as well as mineral oils. These liners are conformable and, when appropriately sized, comfortable and easily donned and removed. Liners fit closely against the skin, and may further be subjected to internal vacuum pressure that ensures a close fit, and if the fit creates an effective seal, may create a subatmospheric pressure internal to the liner. These features contribute to the liner's role in suspension of the prosthetic socket, but they also create a closed environment that supports the buildup of body-generated moisture and heat around the residual limb. Excess heat and moisture are detrimental to the health of the residual limb, as they are damaging to skin integrity and ideal for bacterial colonization.

Although various attempts have been made to remove moisture from prosthetic liners, it has been challenging to remove moisture while still providing adequate suspension force. Thus, improved prosthetic socket liners with moisture management features are still desired.

SUMMARY OF THE TECHNOLOGY

Various embodiments of a moisture management prosthetic socket liner system may include a number of moisture management features as well as methods for removing moisture from the interior of a liner when it is being worn by a patient. Although moisture management features described herein are primarily integrally included within the structure of the liner garment (or "liner" or "liner device"), some aspects of moisture management may also be included in the prosthetic socket itself. Embodiments of the moisture managing liner garment are sized and shaped to accommodate a distal portion of a residual limb. Embodiments of a prosthetic socket frame and a liner garment are mutually sized and configured such that the socket accommodates the moisture managing liner garment. The garment includes an internal surface and an external surface, as well as a proximal portion and a distal portion. The internal surface is that which comes into direct contact with the skin of the patient's residual limb. The external surface of the garment may come into contact with structural elements of the prosthetic socket, or it may be exposed directly to the ambient atmosphere, depending on the particular structure of the socket. The proximal portion of the garment is open to receive the residual limb, and the distal portion is distally closed.

In one aspect, a moisture management liner device for a prosthetic socket may include: an elongate, cup-shaped, elastomeric member, comprising a first material and extending from an open proximal end to a substantially closed distal end, where the substantially closed distal end comprises a fluid exit aperture to allow fluid to pass out of the liner device; and multiple fluid transport strips, comprising a second material and disposed at spaced-apart intervals around a circumference of an internal surface of the elastomeric member, over at least a distal portion of the elastomeric member, where the fluid transport strips are configured to facilitate passage of fluid out of the liner device through the fluid exit aperture.

In some embodiments, the elastomeric member may be a contiguous layer. Some embodiments may further include an array of radially-directed pores extending from the internal surface to an external surface of the elastomeric member. In some embodiments, the array of radially-directed pores is disposed proximal to the longitudinally aligned fluid transport strips. Some embodiments may further include an outer fluid transport substrate disposed over at least a portion of an external surface of the elastomeric member to facilitate passage of fluid out of the liner device through the pores. In some embodiments, the fluid transport strips comprise a wicking fabric. In alternative embodiments, the fluid transport strips comprise a breathable mesh fabric.

In some embodiments, the liner device may further include a valve and/or a pump attached to the device to facilitate unidirectional fluid flow out of the liner device. In some embodiments, the liner device may further include a distally projecting outlet in fluid communication with the fluid exit aperture and a prosthetic socket support element, comprising a centrally positioned annular locking mechanism clampable around the distally-projecting outlet. Optionally, the distally projecting outlet is also in fluid communication with a fluid residing in an interfacing layer between the liner device and a prosthetic socket to which the liner device is attached. In some embodiments, the liner device may further include a reservoir, comprising an inlet into which the distally projecting outlet of the liner device drains and an outlet, comprising a one-way valve biased toward allowing fluid to escape the reservoir. In some embodiments, the liner device may further include a reservoir coupled to the liner device to capture fluid from the device and from an interfacing space between the device and the residual limb and a pump in communication with the reservoir and configured to draw fluid from the reservoir. In some embodiments, at least a proximal portion of the internal surface of the elastomeric member is configured to form an airtight seal with the residual limb.

In another aspect, a moisture management liner device for a prosthetic socket may include: an elongate, cup-shaped, elastomeric member, comprising a first material, an internal surface and an external surface, and extending from an open proximal end to a substantially closed distal end, wherein the substantially closed distal end comprises a fluid exit aperture to allow fluid to pass out of the liner device; a fluid transport substrate disposed over at least a distal portion of at least one of the internal surface or the external surface of the elastomeric member, wherein the fluid transport substrate comprises a second material; and an array of radially-directed pores extending through the elastomeric member from the internal surface to the external surface, to allow fluid to pass out of the liner device.

In some embodiments, a first layer of the fluid transport substrate is disposed on the external surface of the elastomeric member, and at least some of the pores extend through the first layer of the fluid transport substrate. In some embodiments, a second layer of the fluid transport substrate is disposed on the internal surface of the elastomeric layer. Optionally, at least some of the pores may extend through the elastomeric member, the first layer and the second layer.

In another aspect, a moisture management liner device for a prosthetic socket may include: an elongate, cup-shaped, elastomeric member, comprising a first material and extending from an open proximal end to a substantially closed distal end; a fluid transport substrate disposed between the internal and external layers of the elastomeric member along at least a distal portion of the elastomeric member, wherein the fluid transport substrate comprises a second material; and an array of radially-directed pores extending through at least the internal layer of the elastomeric member to allow fluid to pass from an internal surface of the internal layer to the fluid transport substrate. The elastomeric member may include an internal layer, an external layer and a fluid exit aperture at the distal end for allowing fluid to pass out of the device.

In some embodiments, at least some of the pores extend through the external layer of the elastomeric member. In some embodiments, the fluid transport substrate comprises a wicking fabric. Alternatively, the fluid transport substrate may comprise a breathable mesh fabric. Optionally, the device may further include a valve and/or a pump attached to the device to facilitate unidirectional fluid flow out of the liner device.

In another aspect, the liner garment may include an elastomeric portion and a fluid transport substrate portion. These portions may overlap or physically coexist within the fabric of the liner. In some embodiments, the elastomeric portion comprises a substantially contiguous layer, at least in the proximal portion of the garment. In some embodiments, the elastomeric portion is continuous throughout the garment. Embodiments may further include at least one distal fluid exit port disposed within the distal portion of the garment.

In one embodiment of the moisture managing liner, the fluid transport substrate is arranged as longitudinal strips disposed on the internal surface of the distal portion of the liner. The internal surface of the garment disposed between the longitudinal strips includes the elastomeric portion. The fluid transport substrate provides a first fluid escape path, distally directed, from a skin surface of the residual limb to an environment external to the liner garment. Optionally, the first fluid escape path may further include an exit from the liner through the distal exit port.

Some embodiments of a moisture managing liner garment may further include an array of radially-directed pores that penetrate at least the elastomeric portion of the garment. The pores provide a second fluid escape path (in addition to the distally directed fluid escape path noted above) for fluid that accumulates between the residual limb and the garment. The second fluid escape path leads laterally or radially to the external surface of the liner garment. In some embodiments, the array of radially-directed pores is disposed proximal to the longitudinally aligned fluid transport strips.

In some embodiments of the moisture managing liner garment, the fluid transport substrate may also be disposed on the external surface of the garment. In some embodiments, the fluid transport substrate includes a wicking fabric. In other examples, the fluid transport substrate may include a breathable mesh fabric. In various embodiments, the fluid transport substrate may include valves and/or pumps configured to facilitate unidirectional fluid flow toward the external environment. Some embodiments of the fluid transport substrate itself, however, are freely porous to water and do not exert a bias on the directionality of flow within or across the substrate. In other embodiments, the fluid transport substrate may exert a bias on the directionality of flow within or across the substrate.

Embodiments of the moisture management technology may further include features that are associated with or attached to a distal socket structure, such as a distal cup or distal base. The distal socket structure may include a centrally positioned annular locking mechanism that is configured to be clamped around the distally projecting outlet of the drainage port. In some embodiments, the drainage port is in fluid communication with fluid (air and water vapor) that has accumulated in an interfacing layer between the residual limb and the liner garment when a patient is wearing the liner. More particularly, in some embodiments, the annular locking mechanism can clamp around the distally projecting outlet of the drainage port with sufficient strength that the garment and the distal prosthetic socket structure remain securely attached to each other during normal wear. In typical embodiments, the locking mechanism includes a manually operable release mechanism. Embodiments of the locking and release mechanism are configured to be manually operable by the patient.

In some embodiments of the moisture management technology, a distal prosthetic socket structure further includes a reservoir for capturing fluid that passes through the distally-projecting drain. This fluid may be drawn from the fluid transport path facilitated by the wicking substrate of the liner and/or it may be drawn from an interfacing space between the residual limb and the liner. In some embodiments, the reservoir has an inlet into which the distally projecting outlet can drain when the conformable garment is disposed within the prosthetic socket. A one-way valve may be disposed in either the distally projecting drain or the reservoir inlet to bias moisture draining from within the garment liner or the space between the liner and the socket into the reservoir. The reservoir may further include an outlet, which may include a one-way valve biased toward allowing fluid to escape the reservoir.

While some embodiments may take advantage of a passive or gravity driven drainage into the reservoir, some embodiments of the moisture management technology may further include a pump in operable communication with the outlet of the reservoir to draw fluid from the reservoir. In some embodiments, the pump may be electrically powered. In other embodiments, the pump may be mechanically powered, for example by harnessing a small portion of energy provided by body movements of the patient. In one example of a mechanically powered pump used in some embodiments of the moisture management technology, the reservoir includes a mechanism that captures kinetic energy associated with a movement of the patient and directs such energy to drawing fluid from the reservoir.

In some embodiments of the moisture management technology, the internal surface of the proximal portion of the liner garment comprises only the elastomeric portion; i.e., a circumferential internal region at the proximal-most portion does not include a fluid transport substrate. Such elastomeric internal surface is advantageously disposed and adapted to come into sealing contact with a skin surface of the residual limb, such sealing contact being substantially continuous circumferentially around the residual limb. In various of these embodiments, the sealing contact of the liner garment on the residual limb has sufficient integrity to form an environment within the distal portion of the garment that is closed to a proximally sourced influx of ambient air that, absent such sealing contact, could travel distally beneath the proximal portion of the liner.

Some of these embodiments of the moisture management technology may further include an evacuatable reservoir in fluid communication with a reservoir and with the environment within the closed distal portion of the liner. Upon at least a partial evacuation of the reservoir, a subatmospheric pressure is created within the reservoir and within an interfacing layer between the residual limb and the distal portion of liner. The advantageous result of the subatmospheric pressure is to contribute to the stability or adherence of the moisture management garment liner on the residual limb.

Some embodiments of a moisture management liner garment for a prosthetic socket may include pores that provide a direct path for moisture within the garment to the external environment. As described above in the context of the first embodiment, this liner second embodiment is sized and shaped to accommodate a distal portion of a residual limb and to be hosted within a prosthetic socket. The moisture managing garment liner embodiment has an internal surface and an external surface, a distal portion and a proximal portion, an elastomeric portion, and a fluid transport substrate portion that is disposed at least on the external surface of the garment. The elastomeric portion forms a substantially contiguous layer throughout the garment. The elastomeric portion has an array of radially-directed pores that extend into the fluid transport substrate on the external surface. The pores provide a fluid escape path for fluid that accumulates between the residual limb and the liner garment. This fluid escape path leads to the external surface of the liner garment. The array of pores may be dispersed in any suitable pattern and throughout the inner surface of the liner except for a pore-free circumferential region at the proximal boundary of the garment.

In some examples of this moisture management liner embodiment, the fluid transport substrate may be further disposed on the internal surface of the garment. In other examples, the moisture management liner embodiment may further include a distal fluid exit port disposed within the distal portion of the garment.

Some embodiments of a moisture management liner garment for a prosthetic socket may include a fluid transport substrate sandwiched between an internal and an external elastomeric layer. The moisture managing garment liner embodiment has an internal surface and an external surface, and a distal portion and a proximal portion, an elastomeric portion and a fluid transport substrate portion, and a distal fluid exit port disposed within the distal portion of the garment.

In this embodiment, the elastomeric portion is arranged such that at least a portion is disposed on an internal layer and an external layer of the liner garment, and the fluid transport substrate is disposed as a channel between the internal and external elastomeric layers. The fluid transport portion forms a channel, a generally distally directed fluid escape path from a skin surface of the residual limb to an external environment. The internal surface of the liner (the internal layer of elastomer) includes open pores that expose the underlying fluid transport portion disposed between the internal and external elastomeric layers. These pores are included in the fluid escape path of this embodiment. Moisture escapes from the space between the residual limb and the liner by way of these pores and enters the fluid transport substrate channel, whereby it flows distally through the fluid transport substrate, ultimately escaping through the distal fluid exit port.

Embodiments of the technology further include methods of removing fluid from within a prosthetic socket liner. One embodiment of removing moisture or fluid includes providing a prosthetic socket liner with moisture management features and then moving moisture that has accumulated within the liner garment toward the external environment. Several embodiments of a moisture management prosthetic socket liner garment have been described. In brief, such a liner garment includes an internal surface and an external surface, the internal surface circumscribing an interior space; a distal portion and proximal portion; and an elastomeric portion and a fluid transport substrate. The fluid transport substrate forms or is included within a moisture escape path from within the interior of the liner garment to an environment external to the liner garment. Such moisture escape path may be directed to any of (1) the distal portion of the liner garment or (2) radially through the liner.

In some embodiments of the method, prior to the moving step, the method may include donning the liner garment over a residual limb of a patient, and inserting the residual limb with the donned liner garment into the prosthetic socket.

In some embodiments, the liner garment further comprises a drain in the distal portion of the garment liner. With such embodiments, moving moisture from within the liner garment toward the external environment may include moving moisture distally, and through the distal drain.

In some embodiments, the liner garment further comprises an array of pores on the internal surface of the liner garment. With such embodiments, moving moisture from within the liner garment toward the external environment may include moving moisture radially through the array of pores.

These and other aspects and embodiments will be described more fully below, in relation to the attached drawing figures.

DETAILED DESCRIPTION

Embodiments of the disclosed technology include a prosthetic socket liner garment adapted for moisture management and for use in conjunction with a prosthetic socket for a residual limb. Embodiments of the disclosed moisture management technology are typically disposed within a prosthetic socket liner garment. In some embodiments, however, moisture-managing features associated with or incorporated into the garment may also be supported by the prosthetic socket structural components. Prosthetic sockets for which embodiments of the provided socket liner garment are suitable include embodiments of a modular prosthetic socket (as described in US Published App. No. 2013/0123940 and U.S. patent application Ser. No. 14/213,788), as well as any suitable prior art plastic prosthetic socket.

Figure 5:
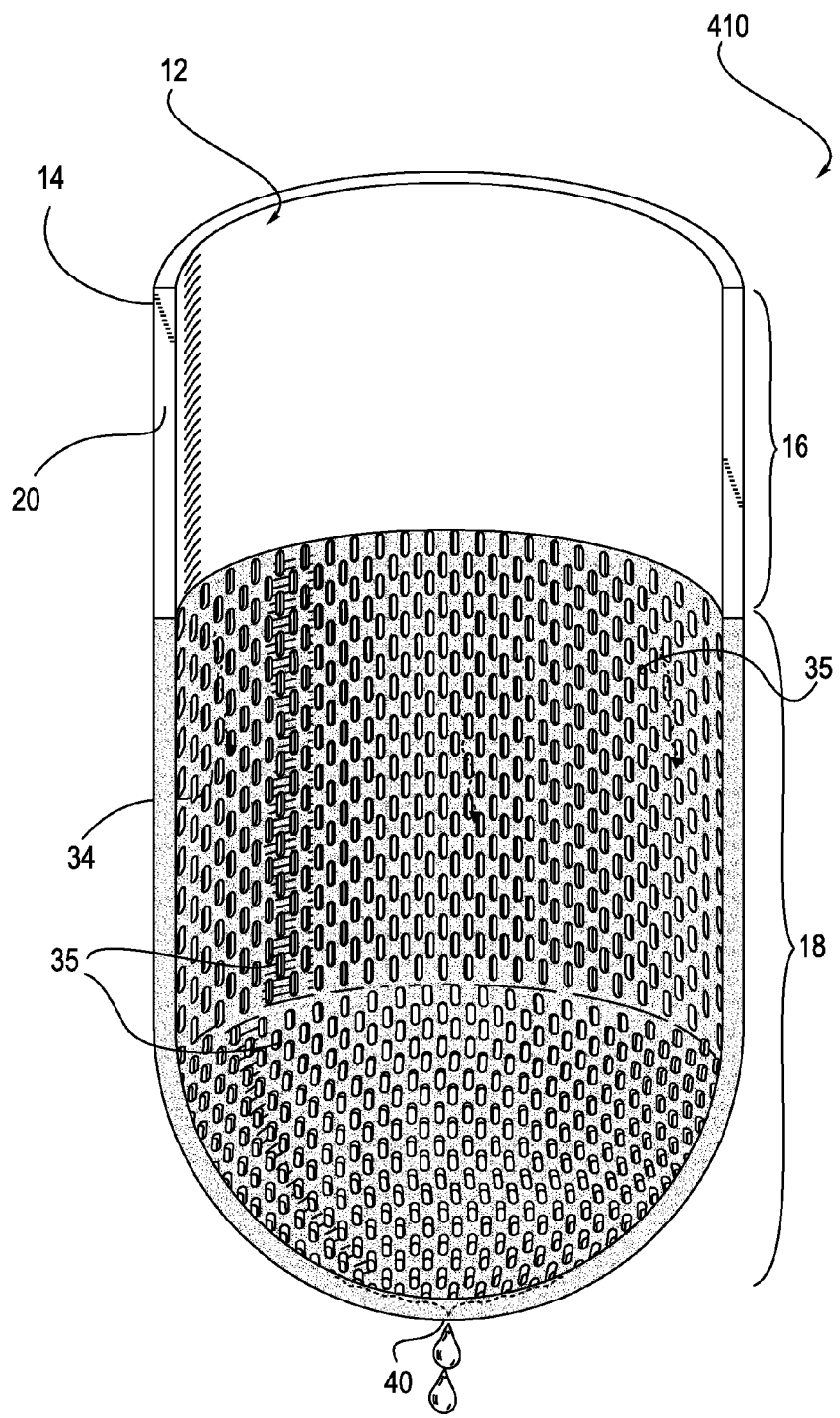
FIG. 5 is a longitudinal cross-sectional view of a prosthetic socket liner that includes a pattern of macroscopic perforations.
Figure 6:
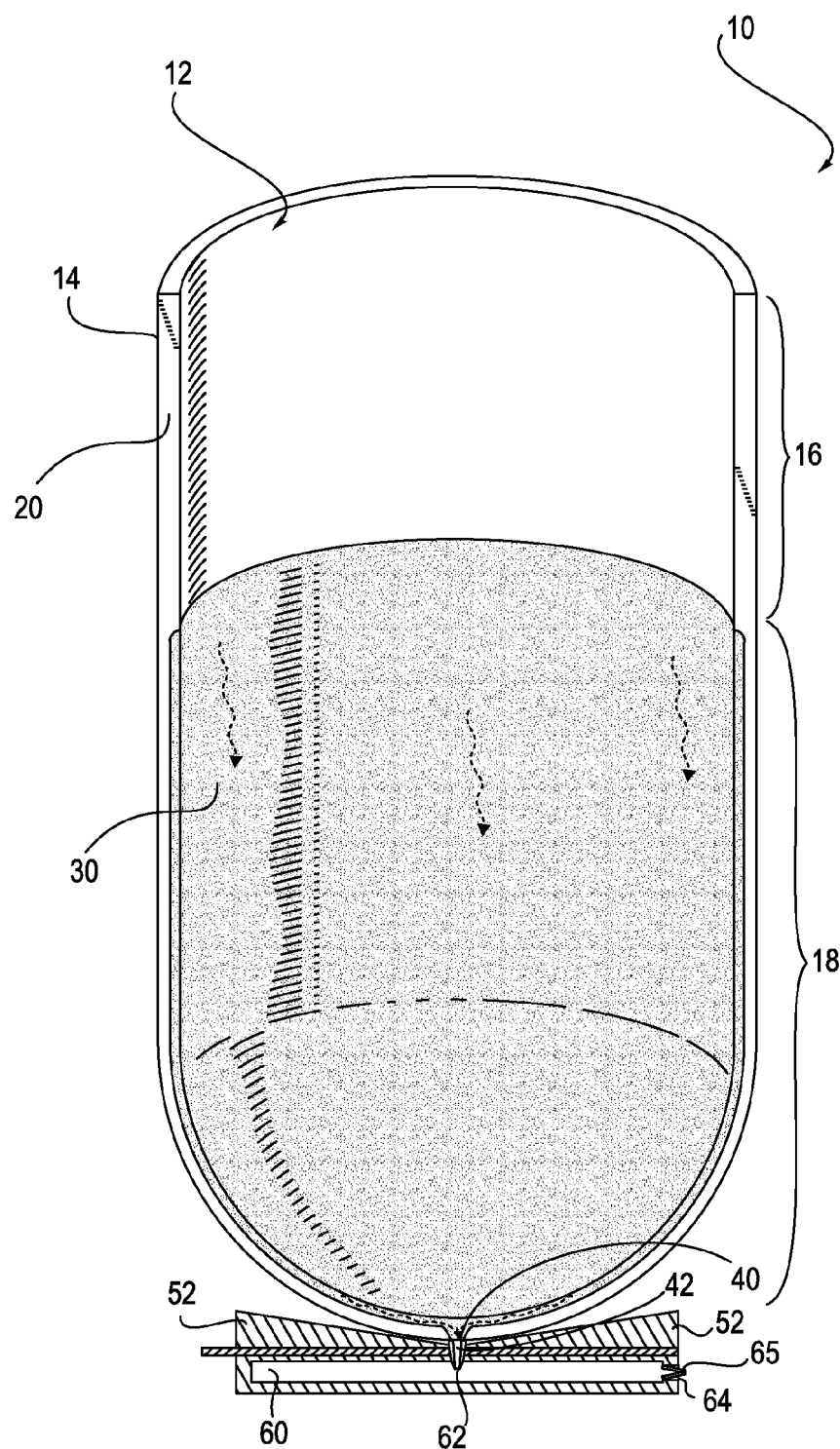
FIG. 6 is a longitudinal, cross-sectional view of a prosthetic socket liner configured to provide a mechanically assisted removal of moisture from within a space between the patient's skin and the surrounding socket, according to one embodiment.
Figure 7:
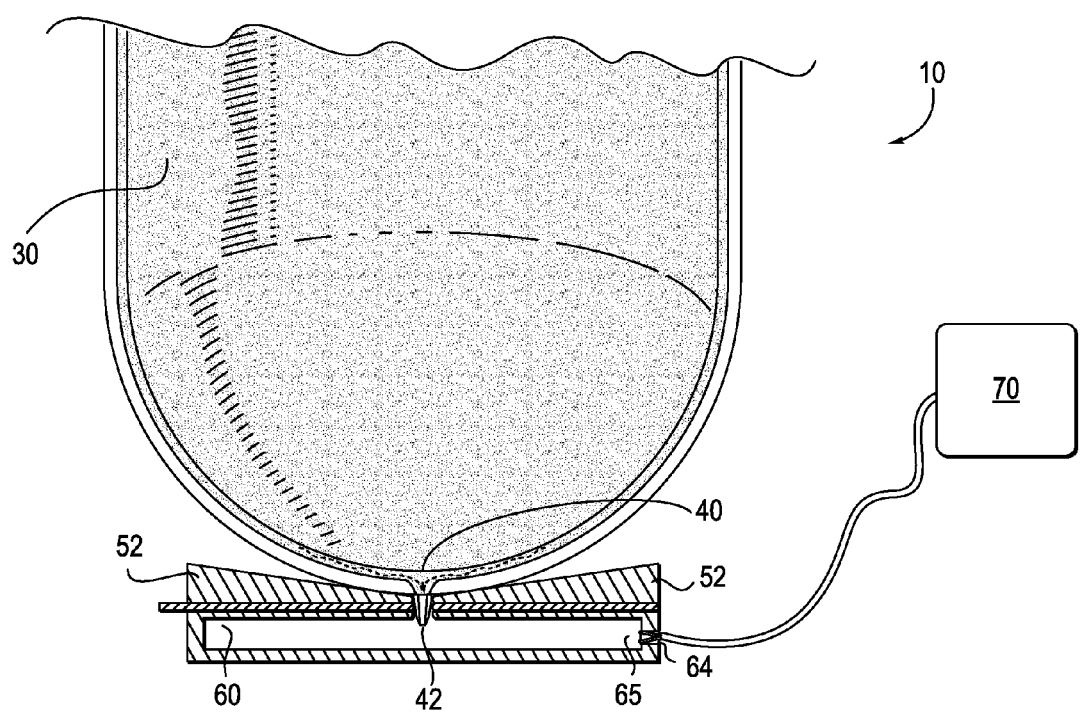
FIG. 7 is a longitudinal, cross-sectional view of a distal portion of a prosthetic socket moisture management liner situated within a socket and including an electric pump driven mechanism that actively withdraws fluid from the reservoir disposed at the base of the socket, according to one embodiment.
Figure 8A:
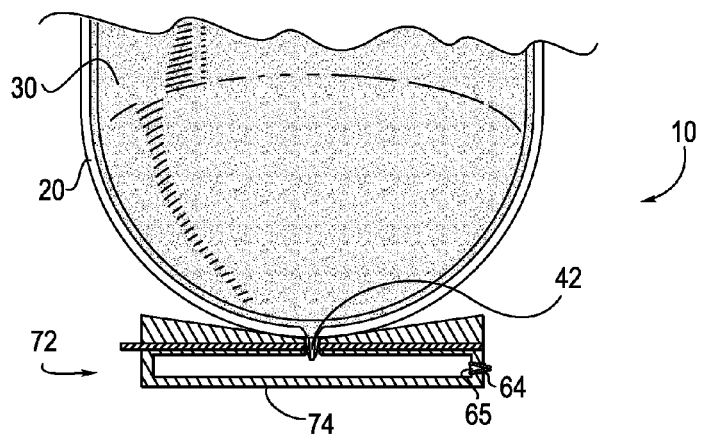
FIG. 8A is longitudinal, cross-sectional view of a distal portion of prosthetic socket moisture management system embodiment situated within a socket that includes a pumping mechanism driven by the impact of a patient's stride, according to one embodiment. This view shows the pump prior to the impact of the leg wearing the prosthesis hitting the ground.
Figure 8B:
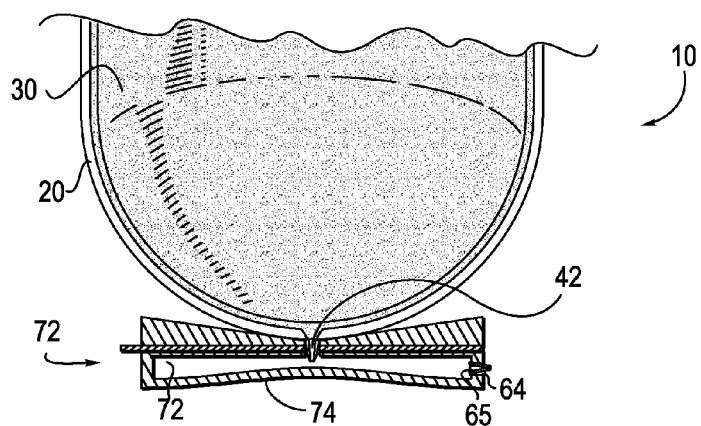
FIG. 8B is view the moisture management system embodiment shown in FIG. 7A at a point during which the stride of a patient is creating an impact that forces compression of a deflectable feature of the pump, the compression causing ejection of accumulated fluid from the pump.
Figure 8C:
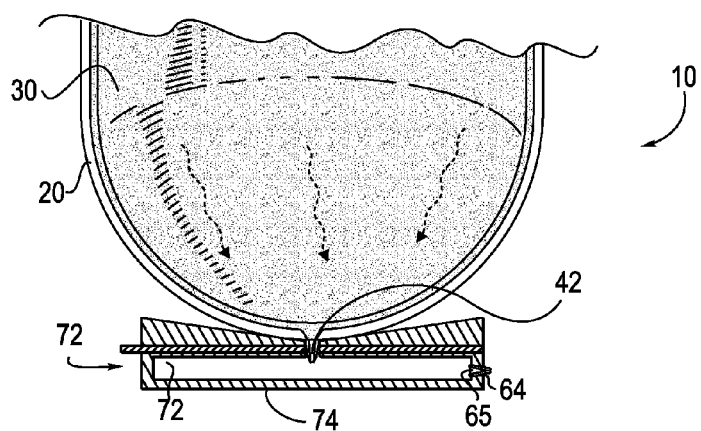
FIG. 8C is view the moisture management system embodiment shown in FIGS. 7A and 7B at a point the leg that created the impact shown in FIG. 7B has now lifted off the ground, allowing the deflectable feature of the pump to return to its undeflected configuration, the pump thereby expanding its internal volume, and drawing in fluid from the distal portion of the moisture management liner.
Figure 13:
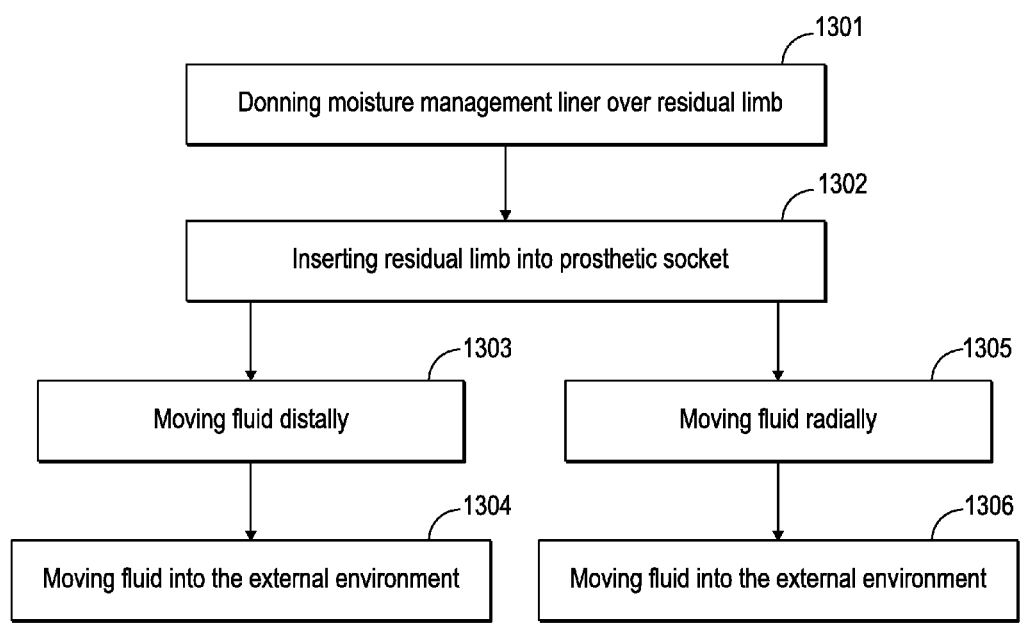
FIG. 13 is a flow diagram of a method of removing accumulated moisture from within a prosthetic socket fitted with an embodiment of a prosthetic socket liner with moisture management features.
Figure 14:
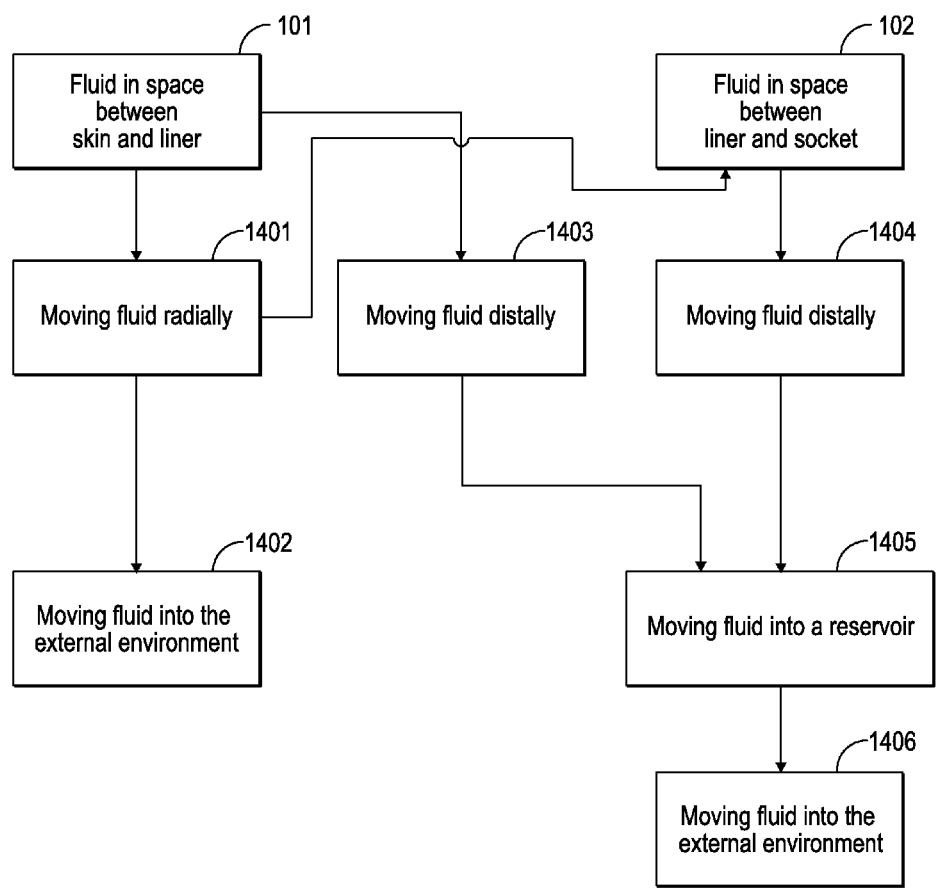
FIG. 14 is a flow diagram of a method of removing accumulated moisture from within a prosthetic socket fitted with an embodiment of a prosthetic socket liner with moisture management features with a focus on fluid flow paths from (1) a space between the skin of the residual limb the liner, and (2) a space between the liner and the prosthetic socket structure.

FIGS. 1-12 show various embodiments of a liner garment that have a similar form factor but vary with regard to their moisture management features. FIGS. 13 and 14 show embodiments of methods of transporting fluid as enabled by embodiments of the moisture management liner. Liner garment 10 (FIGS. 1, 6, and 10) may be considered a basic embodiment. Liner garment 110 (FIGS. 2A-2B) particularly includes fluid transport substrate or wicking strips. Liner garment 210 (FIG. 3) particularly includes lateral pores. Liner garment 310 (FIG. 4) particularly includes both fluid transport strips and lateral pores. Liner garment 410 includes a fluid transport substrate in the form of a breathable fabric. Liner garment 510 (FIGS. 9A-9B) particularly includes wicking channels. FIGS. 7-8C relate to pumping mechanisms that may be applied to multiple garment liner embodiments. Liner garment 10.1 is a generic embodiment of a moisture management liner that calls out no moisture management features in particular, but which is helpful in depicting (FIGS. 11A and 11B) the overall context of the liner in relation to spaces adjacent to it (the space between the liner and the limb, and the space between the liner and a prosthetic socket).

The liner garment embodiments described herein include a proximal portion 16 with an open end and a distal portion 18 with a distal end that is closed except for an optional distal port 40. Proximal portion 16 and distal portion 18 are general terms; the portions need not be sharply demarcated, and the relative site of demarcation can vary from embodiment to embodiment. The liner garment embodiments have an internal surface 12 that interfaces with the surface of a patient's residual limb 90 and an external surface 14 that interfaces either directly with the external environment or an aspect of a prosthetic socket into which the liner garment is disposed. Before describing liner garments 10, 110, 210, 310, 410, and 510 in further detail, the technology will be described in general terms.

Moisture managing liner garment embodiments provide an interfacing surface or space disposed between the skin surface of a patient's residual limb and the socket structure when the socket is being worn. Embodiments of the liner technology include features adapted to reduce or remove moisture that accumulates within the interfacing space between the patient's skin and the socket structure. Reduction or minimization of accumulated moisture occurs by conveying moisture from the interfacing space to the exterior environment by various escape routes, as described in detail below.

Embodiments of the prosthetic socket liner have a central longitudinal axis that aligns (or substantially aligns) with the longitudinal axis of the residual limb on which the prosthetic socket and liner are worn. With reference to the longitudinal axis, embodiments of the liner include a proximal end that is open to receive the residual limb, and a distal end that is closed, to enclose the distal end of the residual limb. Thus, the terms proximal and distal serve as reference terms for the residual limb, for the prosthetic socket, and for embodiments of the liner garment. Further, prosthetic socket liners include an external surface that interfaces either with an inner aspect of the prosthetic socket structure surrounding it, or directly with the ambient atmosphere. Prosthetic socket liners also include an internal surface that interfaces with the skin of the patient's residual limb.

Typical embodiments of prosthetic socket liners described herein are flexible or compliant, fitting the residual limb closely, but in a non-restrictive manner. At least a portion of the internal surface of the socket liner embodiments may have a tacky or sticky aspect that provides a degree of traction against the skin that is sufficient to prevent substantial slippage between the liner and the skin. Another portion of the internal surface may include a fluid transport substrate or channeled features that facilitate the flow of moisture. Flexible and compliant qualities of the liner are such that any embodiment of a liner garment described herein can be donned and everted as described below. A patient donning the liner typically everts the liner, contacts the internal distal-most point of the liner against the distal end of the residual limb, and rolls the liner proximally up the residual limb. Once the initial contact with the residual limb is established, that contact point is maintained as the patient rolls the liner on, converting the everted configuration of the liner into a normal configuration, with the external surface facing outward, and the internal surface facing internally and aligned against the patient's skin. Materials used for the internal tacky surface of the liner may be informally referred to as "gels", and such gels may include any appropriate polymer-based material, such as, but not limited to, urethane, silicon, or thermoplastic elastomer.

Fluid that accumulates in the interfacing space, perspired fluid ("sweat") is similar in composition to plasma, and substantially aqueous. Perspired fluid is liquid, but it gives rise to water vapor. Movement of perspired fluid thus involves movement of water as a liquid and as vapor. In some embodiments, the socket liners described herein may move liquid water by a fluid transport substrate. One example of a fluid transport substrate is a wicking fabric of material. These are materials that readily absorb moisture and facilitate its movement that directionally favors movement from a wetter area to a dryer area. These substrates may include synthetic fibers, such as, by way of non-limiting examples, may include rayon, orlon, or nylon. Fluid transport substrates may further include natural fibers, such as, by way of non-limiting examples, may include wool, felt, hemp, or cotton. These substrates may include any combination of synthetic and natural fibers, and in any available physical configuration and weight. Movement of water vapor similarly may occur by way of vapor movement from a region of higher partial pressure (as within the interfacing space) to a region of lower partial pressure (as in the environment exterior of the socket). Water vapor movement may occur by way of escape through discrete pores, or by way of exit through a porous material.

Routes of moisture escape from the interior space to the external environment may be described with reference to the central longitudinal axis of the liner. Fluid movement may occur in a distal direction, a proximal direction, and/or lateral or radial directions from the space within the prosthetic socket to the exterior environment. In another aspect, fluid may move variously across a wettable substrate, through channels, or directly through pores or a porous interface. Further, fluid movement may be passive, being driven only by gravity or by an equilibrium-driven force applied either to liquid or vapor, and/or it may be mechanically assisted. Mechanically assisted fluid movement may include harnessing of force derived from bodily movement of the patient, or by powered pumps, such as electrical pumps.

In the following description and in the attached figures, a given numerical label may be used to refer to the same component part in different embodiments. For example, a fluid transport portion of a prosthetic liner garment will be shown and described in the context of liner garment embodiments, rather than labeling the different fluid transport portions with distinct numbers. This labeling consistency is used to facilitate understanding of the description and should not be interpreted as suggesting that there is only one embodiment of any given component. Various embodiments of moisture-management liners, prosthetic socket structures that can accommodate such liners, and moisture management devices and methods are described further below, in the context of the drawings.

Figure 1:
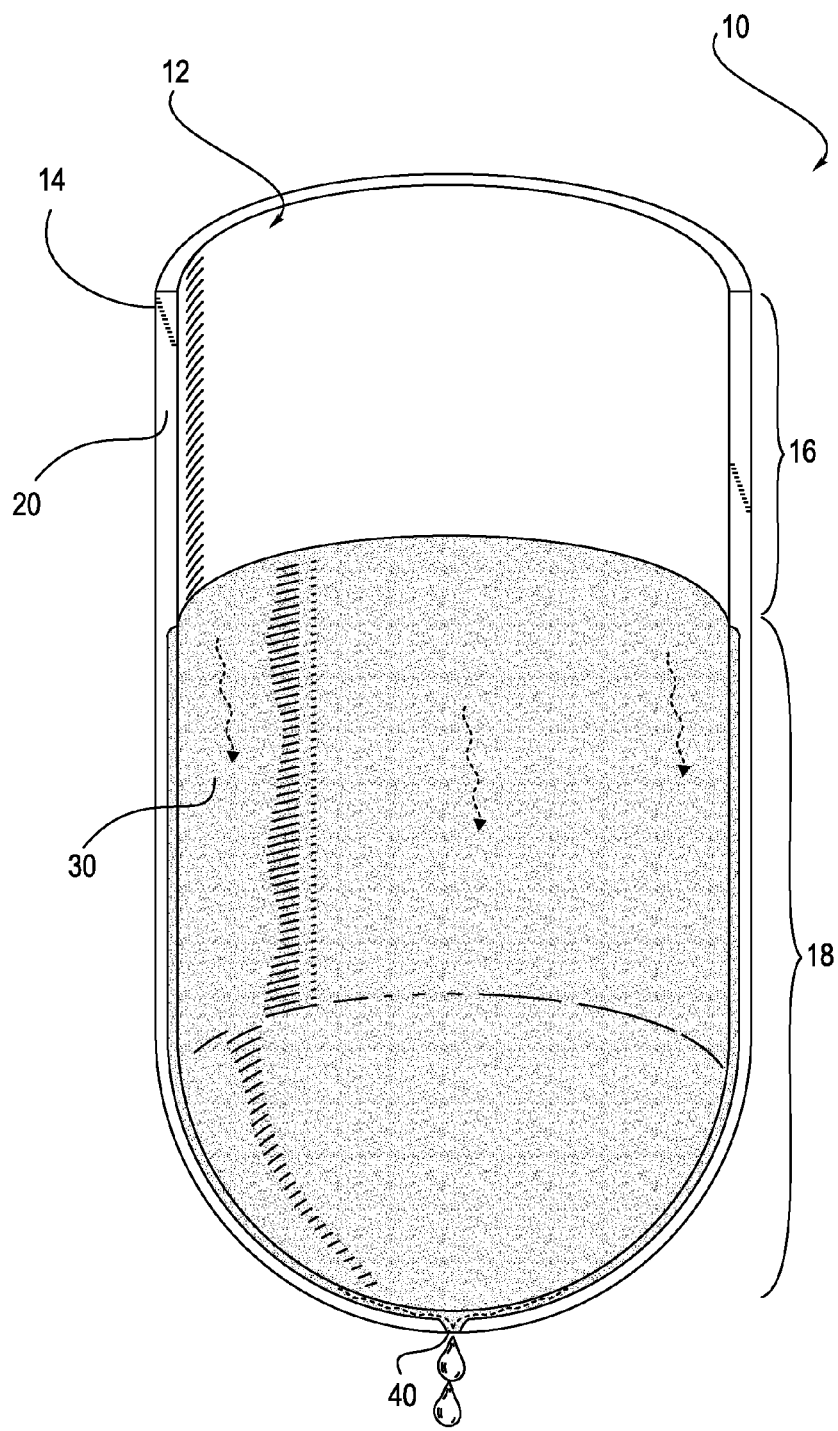
FIG. 1 is a longitudinal cross-sectional (exposed half-pipe) view of a prosthetic socket liner in which the fluid transport substrate is arranged so that its proximal end terminates below the proximal end of the prosthetic socket, according to one embodiment.

FIG. 1 illustrates an embodiment of a prosthetic socket liner garment 10, including a gel portion 20, comprising elastomeric material, and a fluid transport or wicking portion 30. Embodiments of the fluid transport substrate include a wicking material 30 on an internal surface 12 of a prosthetic socket liner 10 to provide a distal-ward flow of moisture (downward-directed arrows) toward a distal fluid exit 40. In this embodiment, wicking portion 30 is disposed only in a distal portion 18 of the liner garment. As such, a wicking fabric or substrate contacts the residual limb in the distal portion of the liner, while an internal surface of the gel portion 20 of the liner contacts the residual limb within the proximal portion 16 of the liner. In some embodiments, a wicking element may also be incorporated into a distal port 40 in order to facilitate fluid movement.

Elements that move moisture distally from the distal port are shown in FIGS. 5-7, as described further below. The wicking-based movement of moisture depicted in some embodiments is not mechanically assisted, and may be passive to at least some degree, although gravity generally is assistive. The socket liner garment 10 may wick moisture substantially derived from perspiration being released from the skin covering the portion of the residual limb disposed within the prosthetic socket, and the socket liner 10 may also wick other forms of moisture that may accumulate between the patient's skin and the liner 10. Forces driving the distal-ward capillary action-based movement of perspired moisture include gravity and a fluid level gradient, wherein there is mass movement of moisture from regions of the wicking material that are heavily laden with water to regions that are drier.

As shown in FIG. 1, in some embodiments, the wicking material 30 is arranged so that its upper or proximal end terminates below the proximal end of the prosthetic socket liner garment 10, the proximal portion of the liner having only the elastomeric or gel portion 20.

Figure 2A:
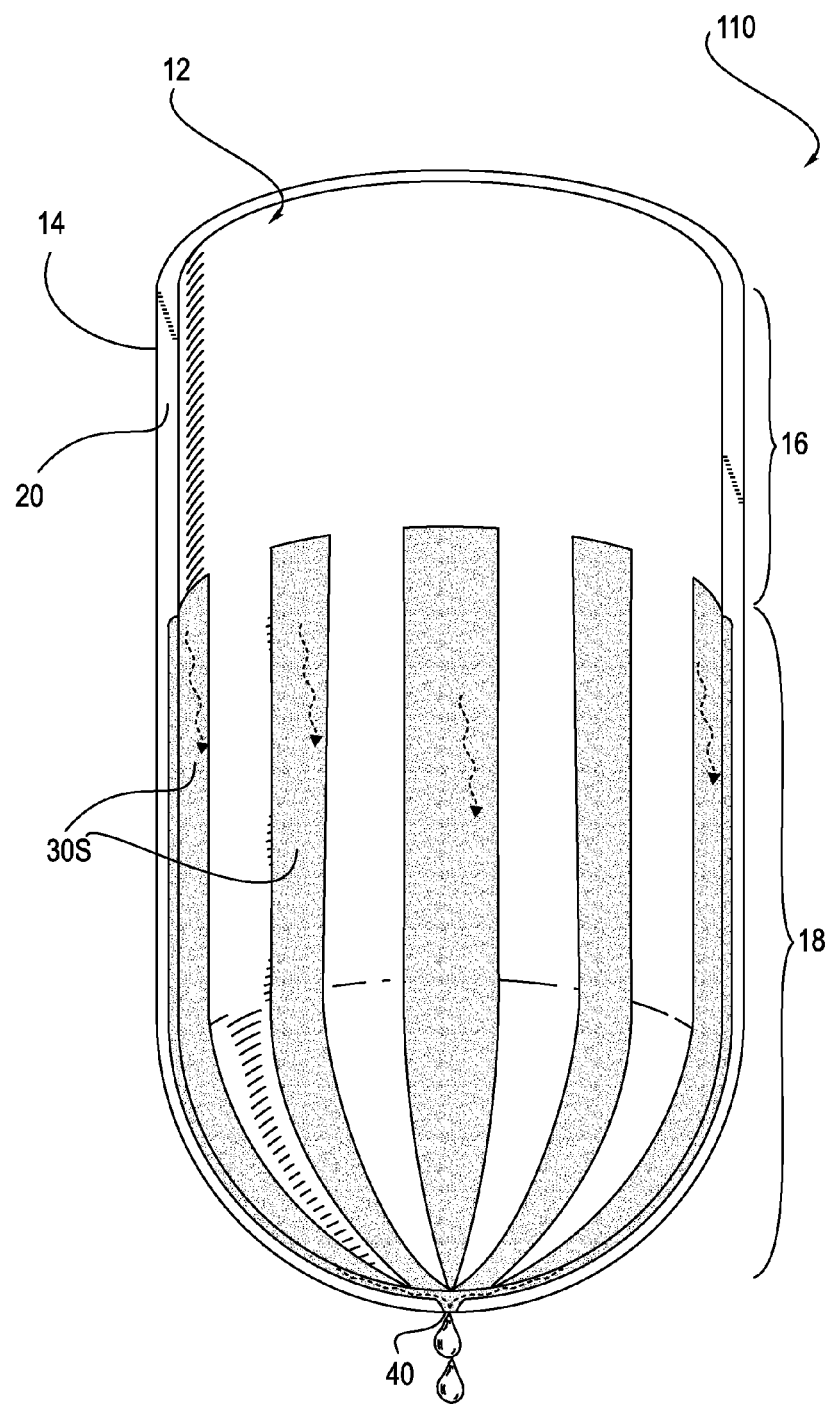
FIG. 2A is a longitudinal cross-sectional view of prosthetic socket liner in which the fluid transport substrate is arranged into longitudinal strips, the strips distributed circumferentially such that they are spaced apart, according to one embodiment.
Figure 2B:
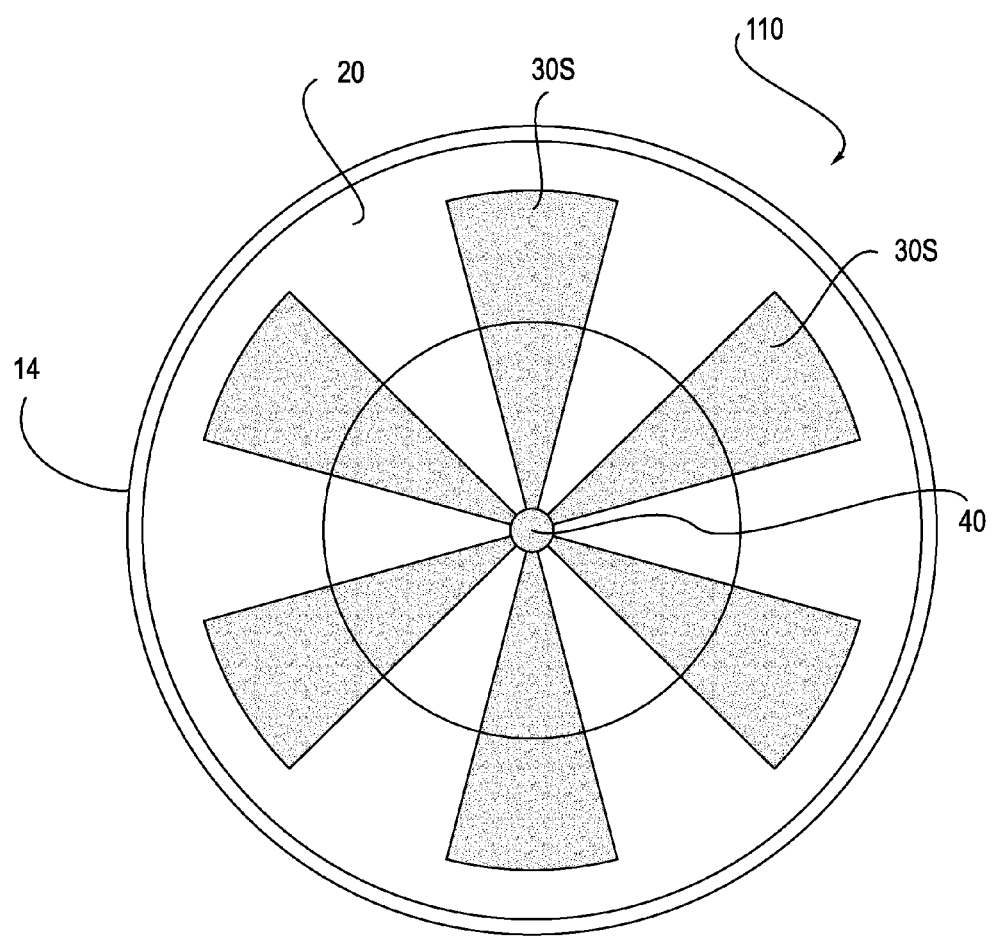
FIG. 2B is a top view of the prosthetic socket liner shown in FIG. 2A, looking proximally into the distal end of the liner, in which the fluid transport substrate is arranged into longitudinal strips, the strips distributed circumferentially such that they are spaced apart.

FIGS. 2A and 2B illustrate an embodiment of a socket liner garment 110 similar to that shown in FIG. 1, except that the fluid transport substrate or wicking material 30 is arranged into longitudinal strips 30S distributed circumferentially and spaced apart. From an internal perspective, the internal surface or aspect 12 of the liner garment 110 includes longitudinally aligned zones, the zones comprising alternating gel surfaces and wicking material surfaces, each having its own respective functionalities and advantages. The tacky gel material in the distal region of the liner has sufficient surface area to establish a non-slipping engagement of the moisture management liner against the skin of the distal end of the residual limb. The gel surface further serves to facilitate smooth roll-on donning by virtue of its consistency and pliability. The tackiness of the gel layer further serves to facilitate a stability of the garment on the surface of the skin, generally mitigating against slippage or buckling that could allow air to enter into the space from under the proximal boundary of the liner. The wicking strips serve to move moisture in along a moisture gradient and gravity-driven direction that is generally distal, toward distal fluid exit 40.

FIG. 2B is a distal-looking internal view of the liner garment 110 of FIG. 2A, where the longitudinally arranged strips of fluid transport substrate or wicking material 30S taper from a relatively large width at their proximal end to a relatively narrow width at their distal end as they converge centrally and terminate proximal a distal fluid exit 40. Fluid thus can move distally by way of capillary action, and exit the internal environment within the liner distally.

In the embodiments shown in FIGS. 1, 2A, and 2B, the wicking fabric or fluid transport substrate 30 does not extend proximally to the most proximal edge of the socket liner garments, as in garment embodiments 10 and 110. Thus, some embodiments of the socket liner garment are arranged such that a wicking material 30 on the interior surface has an upper or proximal edge that terminates at a level below that of the upper or proximal edge of the liner as a whole. In these embodiments, the proximal portion of the gel portion 20 of socket liner garment 10 and 110 thus directly contacts the skin of the residual limb, and can broadly form a seal against the skin that creates a substantially closed environment within the confines of the distal portion of the socket liner garment 10 and 110. The closed distal environment of these embodiments allows egress of water by way of the distal drain. While the movement of moisture in these depicted embodiments is passive, in other embodiments, moisture can be actively pulled or pushed out through the distal drain.

In some embodiments, the wicking substrate portion is attachable to, and detachable from, the elastomeric portion of the liner garment. This arrangement is advantageous, in that it allows the liner garment to be embodied in two pieces, a portion that is elastomeric or substantially elastomeric, and a separate wicking piece that can either be rinsed clean and reattached to the elastomeric portion of the liner, or be replaced by a new wicking piece.

Figure 3:
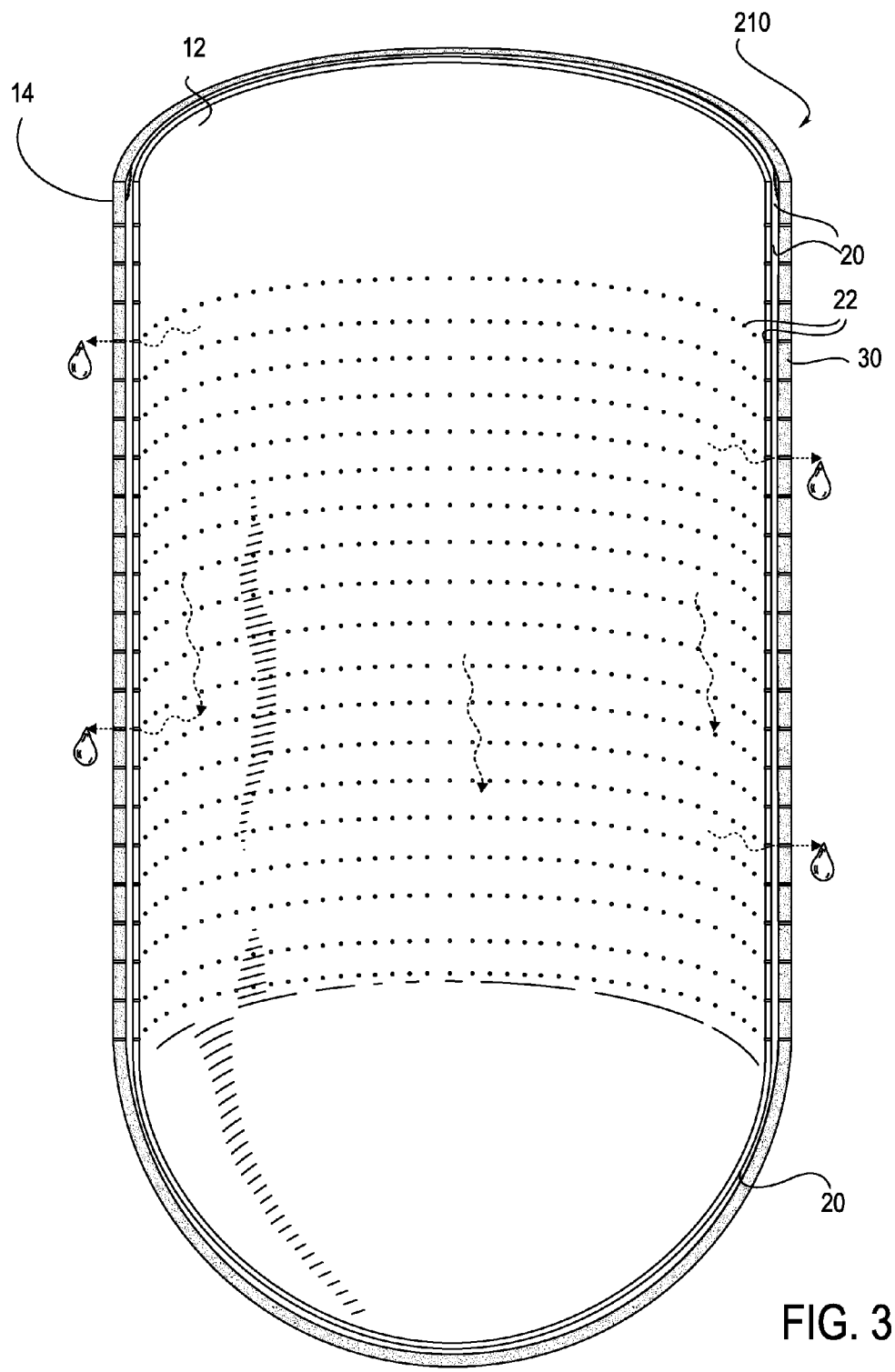
FIG. 3 is a longitudinal, cross-sectional view of a prosthetic socket liner configured to provide for the escape of water vapor in a lateral or radial direction with respect to the longitudinal axis of the liner, according to one embodiment.

FIG. 3 is a longitudinal cross sectional cutaway view of another alternative embodiment of a prosthetic socket liner garment 210 that is arranged to provide for the escape of water vapor in a lateral or radial direction with respect to the longitudinal axis of the liner. Such escape may occur through pores or ports 22 that may be microscopic or scarcely visible within a fabric, or a generally porous site. (Pores may be generally distinguished from discrete macroscopic formed apertures, such as described further below in the context of FIG. 5.) Such pores or ports 22 may be distributed within or on a liner surface comprising a gel. As moisture is brought to the external surface of the gel liner, it has the opportunity to evaporate. Such evaporation, in addition to providing an escape path for moisture, may also advantageously cool the surface of the liner, and such cooling may, in turn, cool the surface of the portion of the residual limb contained within the prosthetic socket. Aside from evaporative cooling, such pores may also provide a path for draining heat from the environment interior to the socket liner. Heat may be drained simply by the conveyance of heat by escaping moisture, which has been heated by the body.

Figure 4:
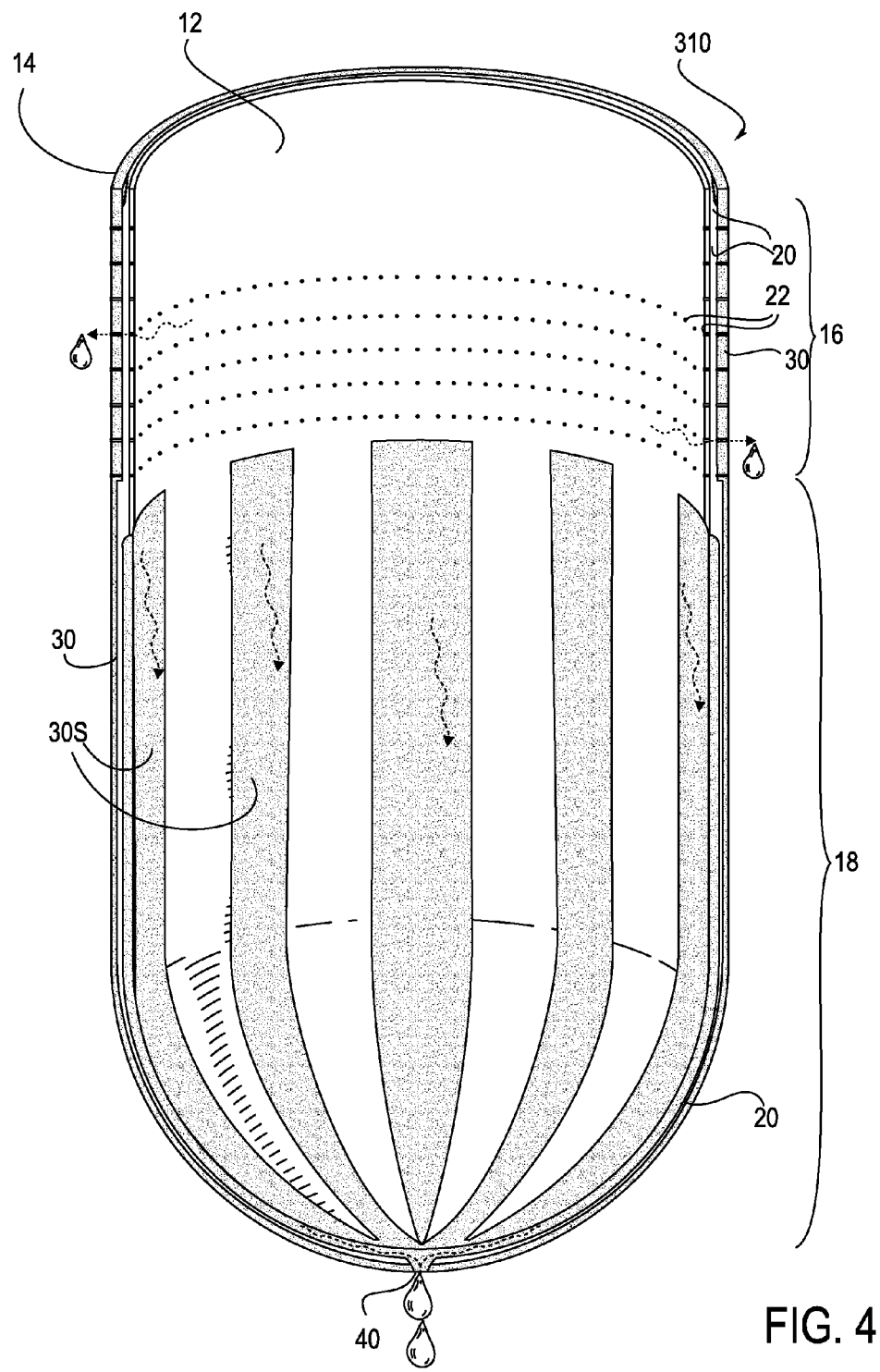
FIG. 4 is a longitudinal, cross-sectional view of a prosthetic socket liner configured to provide both for distal movement of moisture and also for lateral or radial escape of moisture, according to one embodiment.

FIG. 4 shows a longitudinal cross sectional cutaway view of a prosthetic socket liner garment embodiment 310 that is arranged to provide both for distal movement of moisture (as shown in FIGS. 1-2B) and for lateral or radial escape of moisture (as shown in FIG. 3). Description of these aspects of the embodiments in the context of those referenced figures applies to the embodiment 310. The fluid transport portion 30 of this embodiment is disposed both internally and externally with respect to elastomeric portion 20. The internally arranged fluid transport portion is labeled 30S to indicate it being arranged as longitudinal strips. Fluid transport substrate or wicking material 30S is arranged into longitudinal strips on the internal surface 12 of the distal portion 18 of liner garment 310, and the strips are distributed circumferentially and spaced apart. The internal surface 12 of proximal portion 16 of liner garment 310 includes a region that has pores 22 or perforations that extend through to external surface 14. The most proximal region of internal surface 12 has no pores, the uninterrupted elastomeric surface being optimal for forming a sealing engagement against a residual limb.

FIG. 5 is a longitudinal cross-sectional view of a prosthetic socket moisture management liner 410 that has a fluid transport portion 34 in the form of a fabric having mesh pattern of macroscopic apertures or perforations in distal portion 18 of the garment. The fluid transport portion 34 of this particular embodiment comprises a three-dimensional knit or woven structure that provides breathability by way of macroscopic apertures 35 formed by the knit or weave. At least the internal surface 12 of the proximal portion 16 of the liner garment 410 includes a gel or elastomeric portion 20 that provides a tacky surface that provides a sealing contact with the skin of the residual limb. In this particular liner garment embodiment 410, the elastomeric portion does not necessarily extend into the distal portion 18 of the liner. The thickness or weight of the yarn or fiber used in the knit or weave of mesh can vary, and there is a general correlation between fiber thickness and the size of the apertures of the mesh. In some embodiments, the apertures are formed only by the space between fibers. In other embodiments, the apertures are larger formed structures within the fabric.

The fibers within the mesh can vary in composition. For example, at least some fibers may be coated with a composition that provides a tackiness that encourages adherence to the skin; at least some fibers may be particularly suitable for supporting capillary movement of moisture; and at least some fibers may be elastic to encourage a close and conformal fit to the residual limb. The apertures in the mesh may be large enough to provide direct ventilation through the mesh, moisture as a liquid or vapor moving freely through the mesh. The fibers of the mesh may support wicking from inside the garment to the exterior, whereupon the moisture can evaporate. In some embodiments, the apertures may include structural features that bias net moisture flow in the internal to external direction, in a one-way valve like manner.

FIG. 6 shows a longitudinal cross sectional cutaway view of a prosthetic socket liner garment embodiment 10 that is arranged to provide a mechanically-assisted removal of moisture from within the interfacing space between the patient's skin and the surrounding socket. In this particular embodiment, the upper or proximal-most edge of a wicking substrate within the moisture management liner terminates at a level below the upper or proximal-most edge of the liner garment 10 as a whole. In the zone of the liner proximal to the wicking fabric or substrate, the liner comes directly in contact with the skin of the patient's residual limb. Inasmuch as the internal liner surface exposed to the skin is tacky, it tends to form a seal against the skin, and accordingly, the interfacing space between the liner and the skin may be understood as a closed environment. The route of escape for accumulated moisture is by way of a drain at the distal end of the liner.

This embodiment of the liner is situated within a distal portion of the prosthetic socket structure 5 that includes an annular locking mechanism 52 that secures the socket and liner together by clamping around the drain or associated structure. This connection, in a larger functional sense, provides a prosthetic socket suspension mechanism that prevents the socket from slipping off the residual limb: the gel liner hangs on to the residual limb, the gel liner and distal prosthetic socket structure are locked together, and distal prosthetic components are connected to the distal prosthetic socket structure. Aspects of the suspension mechanism include both a vacuum that is in place and prevents expansion of the interfacing space by the vacuum pressure, as well as by the locking mechanism itself.

The distally projecting drain 42 leads into a reservoir 60 disposed proximate the distal base such that fluid flows from the interfacing space, through the drain, and into the reservoir, which, itself has a controllable effluent opening, such as a one-way valve 65 that allows one-way efflux of accumulated moisture.

FIG. 7 is a longitudinal cross sectional cutaway view of a distal portion of prosthetic socket moisture management liner embodiment 10 situated within a socket embodiment that is similar to that depicted in FIG. 6. Although liner garment 10 is used in FIGS. 6-8C, any liner embodiment having a distal drain may be fitted with a reservoir 60. Whereas the embodiment shown in FIG. 6 may be considered a passive moisture management approach, driven by gravity and gradient dynamics, the embodiment shown in FIG. 7 provides an active or powered moisture management approach, as driven by an electric pump 70 that actively withdraws fluid from the reservoir disposed at the base of the socket.

FIGS. 8A-8C are longitudinal cross sectional cutaway views of a distal portion of prosthetic socket liner embodiment 10 situated within a socket embodiment that is similar to that depicted in FIG. 6, but having a reservoir 72 that acts as pumping mechanism driven by patient movement, rather than electrical power. FIG. 8A shows pumping reservoir with fluid exit through outlet 64, as controlled by a one-way valve 65. The lower surface or plate 74 of pumping reservoir 72 is resiliently deflectable from a resting position to a deflected position. This deflectable feature is but one example of an inwardly movable portion, which upon application of external pressure, deflects inward, reducing the volume of the reservoir. Movement of the patient, as in walking or shifting body weight, provides the episodic force for such inward movement. FIG. 8B shows such an inward deflection of resilient plate 74, and the consequent reduction in volume or increase in pressure that drives fluid through the one-way valve 65, thus exiting the reservoir 72. Upon release of the patient-applied pressure, the lower plate of pumping reservoir 72 resiliently returns to its resting position. In returning to its resting position, either completely or partially, the resting volume of the reservoir 60 is restored toward normal, but the pressure within the reservoir 60 is lowered. Such lowered pressure, as seen in FIG. 8C, exerts a vacuum pull on the liquid proximal to the drain connecting the skin-liner interfacing space to the reservoir 72.

The optional mechanically assisted aspect of moisture flow mechanism is similar to the embodiment shown in FIGS. 8A-8C, insofar as the patient provides the mechanical force. This embodiment harnesses patient movement as it occurs within the socket, particularly as transmitted against the wall of the socket, rather than the weight bearing distal end. With each step or movement made by the patient, there can be a change in the laterally directed pressure against the wall. Regions of relatively high pressure, which may exist only transiently, will force perspired fluid into the relatively low-pressure zone occupied by the wicking layer. Once in the wicking layer, fluid will be driven distally by gravity. In some embodiments, the wicking layer may include valves, such as deflectable flaps, that preferentially drive liquid in a distal direction, thereby taking further advantage of mechanical force provided by patient movement.

In particular embodiments of the moisture management technology, the reservoir can achieve and maintain a subatmospheric pressure when being evacuated by the pump. In these embodiments, the subatmospheric pressure of the reservoir, being in communication with fluid (any of air, liquid water, and water vapor) residing in an interfacing layer disposed between the residual limb and the liner, can draw the fluid in from the layer, thereby creating a subatmospheric pressure between the liner and the residual limb. The interfacing layer typically contains a very small volume that can be taken to subatmospheric pressure. One source of such volume may be a fluid transport substrate layer, itself, as associated with the liner or effectively included within the fluid space. Some embodiments of a fluid transport substrate can be compressible and resilient, in which case subatmospheric pressure would cause compression of the fluid transport substrate.

In some of these particular embodiments, the subatmospheric pressure created within the layer between the residual limb and the liner contributes to the stability or maintenance of the liner on the residual limb. In some of these particular embodiments, the garment liner may be physically connected to the prosthetic socket, and the subatmospheric pressure within the interfacing layer may contribute to maintaining the socket on the residual limb, a capacity generally known as "suspending" the prosthetic socket. In this context, "suspending" refers to holding the prosthetic socket onto the residual limb such that it does not passively or inadvertently slip off.

Figure 9A:
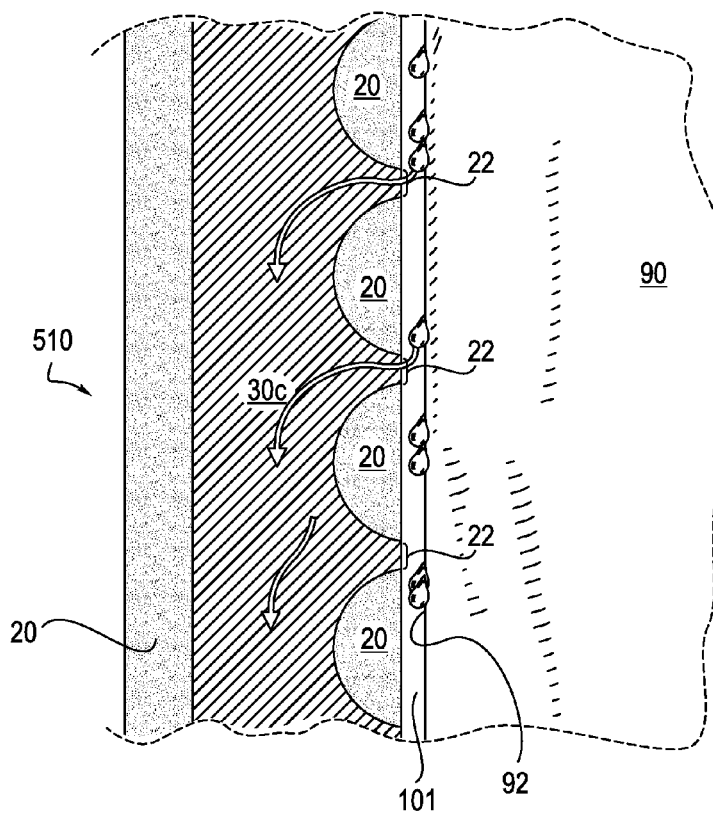
FIG. 9A is a longitudinal cross sectional view of a length of a prosthetic socket moisture management liner embodiment that includes a layer of fluid transport substrate sandwiched within a larger gel layer.
Figure 9B:
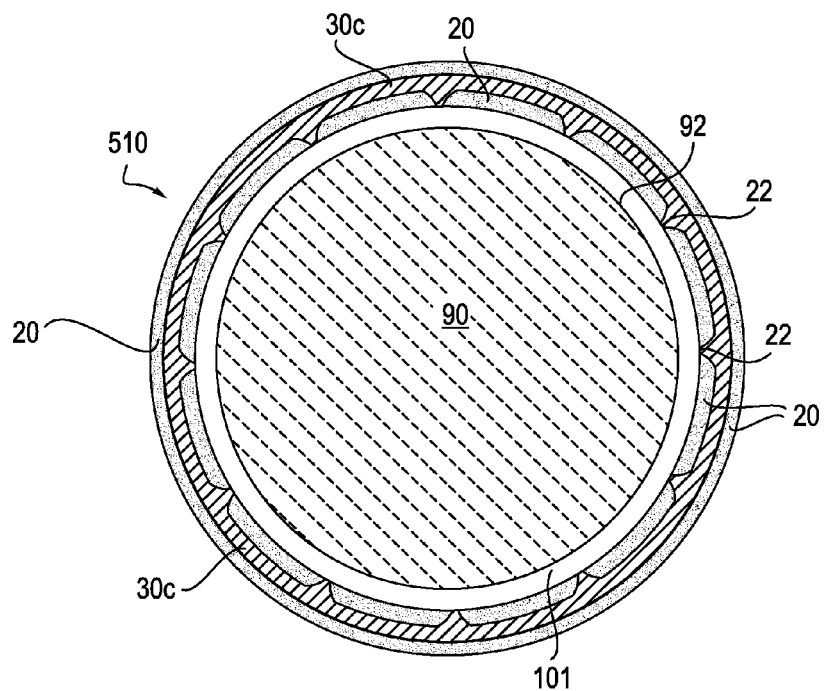
FIG. 9B is a cross-sectional view of the prosthetic socket moisture management liner shown in FIG. 9A.

FIGS. 9A and 9B are longitudinal and radial cross sectional views, respectively, of an embodiment of a prosthetic socket liner garment 510 with a layer of fluid transport substrate or wicking material in the form of a channel or layer 30C sandwiched between internal and external gel or elastomeric layers 20. The inner elastomeric layer 20 includes an array of pores 22 that provide fluid access to fluid transport substrate embodiment 30C. The overall form of liner garment 510 is the same as seen in FIGS. 1-5, variously depicting other embodiments 10, 110, 210, 310, and 410, each having different arrangements of elastomeric portion and fluid transport substrate.

In liner garment 510, the fluid transport substrate and elastomeric portion 20 cooperate to form a fluid transport or wicking channel 30C. The liner garment 510 is shown as being worn by a patient and his or her residual limb 90. An interfacing layer or space 101 is located between the skin of residual limb 90 and internal surface 12 of liner garment 510. FIG. 9A shows a longitudinal cross sectional cutaway view of a side portion of a prosthetic socket moisture management liner embodiment situated within a socket embodiment; FIG. 9B shows an end-on/cross-sectional view. This particular embodiment includes aspects of both passive moisture flow in a distal direction and an optional mechanically assisted flow, as shown in FIGS. 7-8C. The moisture management liner embodiment 510 depicted here includes one or more fluid transport channels 30C. The channel is shown disposed between the inner and outer gel layers 20 (on the left) and the skin surface of patient's residual limb 90 on the right. At spaced apart locations, the internal surface of gel layer has pore openings 22 that allow fluid transport channel 30C to contact the patient's skin or interfacing space 101 directly. These openings 22 represent pores or ports through which perspired fluid can flow into the main body of the fluid transport layer 30C.

The fluid transport channel 30C does not need to be circumferentially continuous. In some embodiments (not shown), inner and outer gel layers 20 may converge into a single layer, without an intervening fluid transport layer 30C. Accordingly, in some embodiments of moisture management liner garment 510, the fluid transport layer may have a longitudinal strip configuration similar to that of embodiment 110 (FIG. 2A), albeit sandwiched between gel layers 20.

Figure 10:
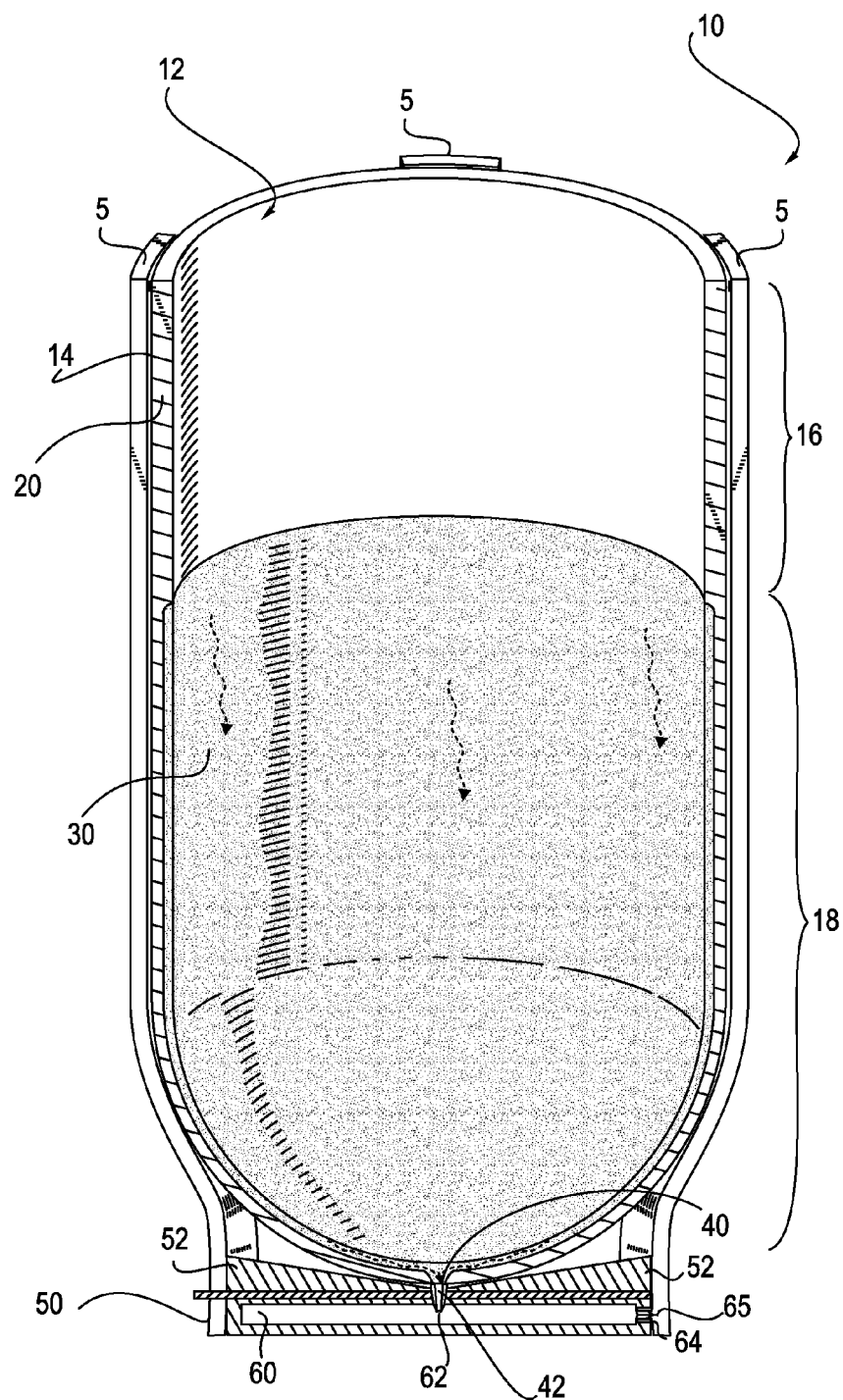
FIG. 10 is a partial, cross-sectional view of a moisture management system disposed in a prosthetic socket frame and a socket liner, according to one embodiment.

FIG. 10 shows a prosthetic liner garment embodiment 10 disposed in a prosthetic socket device or framework. A prosthetic socket is not shown in its entirety in FIG. 10, but it is represented by prosthetic socket struts 5 and a distal prosthetic structure 50, both of which may serve as support elements of the moisture management system provided herein. These prosthetic socket components are consistent with modular prosthetic socket embodiments as described in US Published App. No. 2013/0123940 and U.S. patent application Ser. No. 14/213,788 Annular locking mechanism 52 can be supported by any suitable support element in the proximal region of the prosthetic socket, such as a strut, a distal base, or a distal cup. Such detail is omitted from drawing for the sake of clarity. Although the prosthetic liner garment 10 is shown securely disposed within a modular prosthetic socket, as referenced, many available prosthetic sockets are perfectly appropriate for hosting moisture management liner garments, as disclosed herein.

Figure 11A:
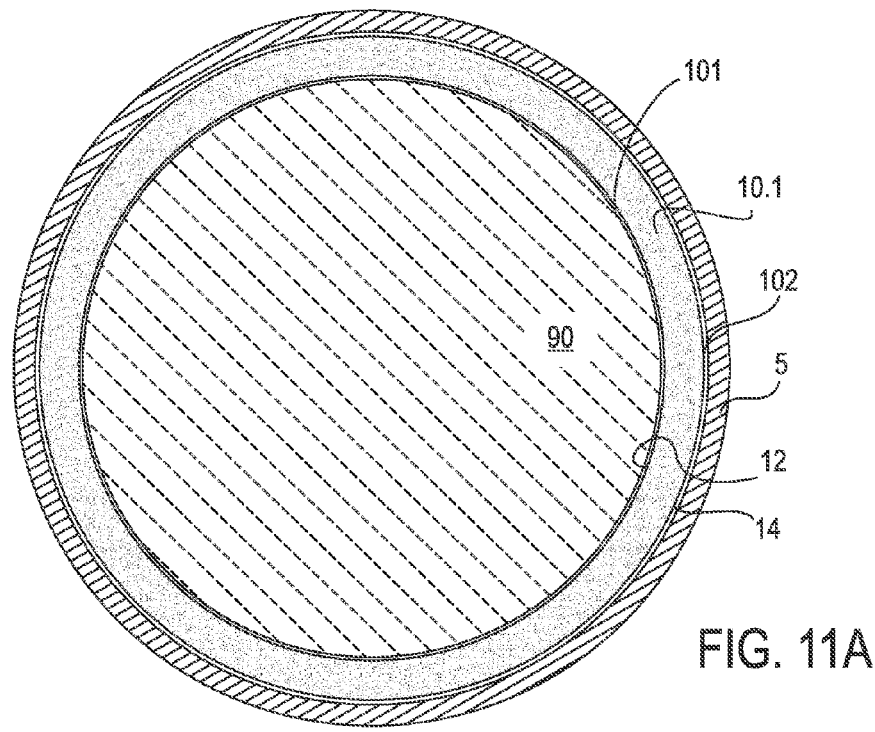
FIGS. 11A-11B are schematic representations of cross-sectional views through a residual limb, a first intervening space, a moisture management liner, a second intervening space, and a prosthetic socket.
Figure 11B:
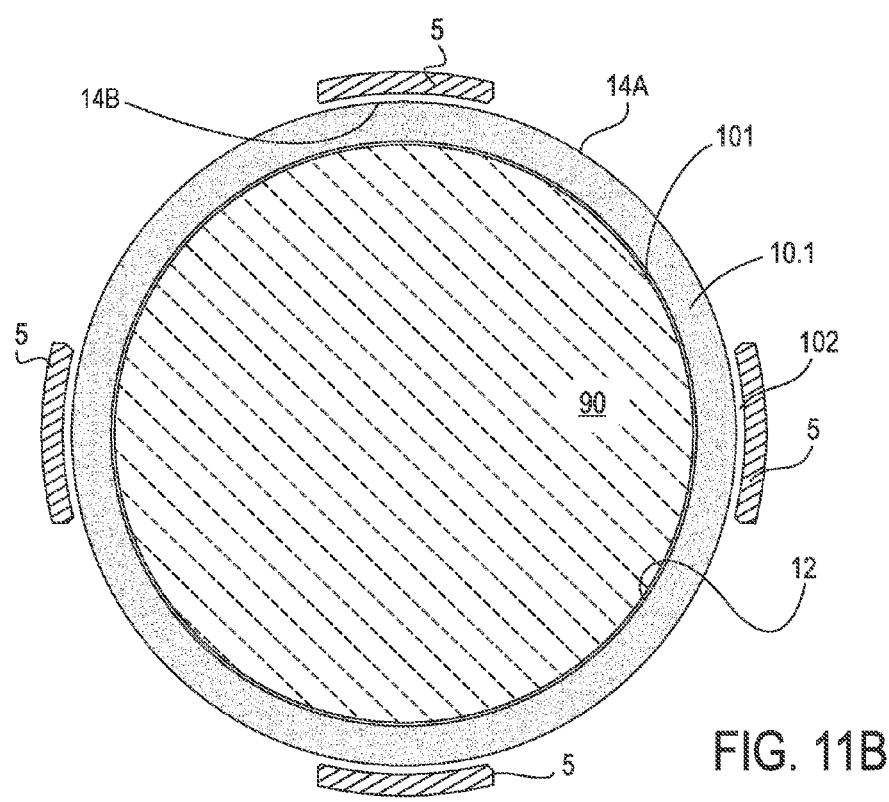

FIGS. 11A-11B are schematic representations (not drawn to scale) of cross-sectional views through (progressing outward from the center) a residual limb 90, a space 101, a moisture management liner 10.1, a space 102, and a prosthetic socket 5. Moisture management liner 10.1 is intended to represent any moisture management liner embodiment as described herein. The focus of FIGS. 11A and 11B is not directed to any particular aspects of a moisture management liner 10.1, but rather to identify and distinguish spaces 101 and 102. Space 101 is disposed between the residual limb and the moisture management liner; space 102 is disposed between the moisture management liner and the prosthetic socket. Neither space 101 nor space 102 is an open void; typically these spaces are collapsed or flattened, but they are both sites where fluid may accumulate or be trapped. In general, it is advantageous for the patient, and for the function of both the prosthetic liner and for the prosthetic socket, that fluid (liquid or gas) be minimally present in these spaces.

Prosthetic socket 5 is intended to represent any prosthetic socket; sockets vary in form, and can vary in their cross sectional profile depending on where the cross sectional view is taken between the proximal and distal ends. Accordingly, FIG. 11A depicts a prosthetic socket (or a longitudinal region thereof) wherein the socket structure is circumferentially complete or contiguous. FIG. 11B depicts a prosthetic socket (or longitudinal region thereof) where the prosthetic socket is circumferentially segmented or discontinuous. Examples of a prosthetic socket such as that depicted in FIG. 11B include modular, strut-based prosthetic sockets as disclosed in US Published App. No. 2013/0123940 and U.S. patent application Ser. No. 14/213,788.

Prosthetic moisture management liner 10.1, as shown in FIG. 11A, has an internal surface 12 and an external surface 14. Prosthetic moisture management liner 10.1, as shown in FIG. 11B, has an internal surface 12 and an external surface that can be separated into regions 14A and 14B. The actual surfaces may be identical, but the environments they face are different. Surface region 14A is directly exposed to ambient air. Surface region 14B is exposed to an inner aspect of strut or strut segment 5, and accordingly, is contained within space 102 (between the liner and the socket). Radial movement of moisture through garment liner 10.1 across surface 14A allows moisture to escape directly into the environment, while radial movement of moisture through liner garment 10.1 across surface 14B would leave it accumulating within space 102.

Space 101, between a residual limb and a prosthetic socket liner, is the site into which sweat from a residual limb can accumulate. Removal of moisture from this site (101) is advantageous for the integrity of the skin and underlying tissue of the residual limb, as well as general comfort and fit. Accumulation of moisture in this space can allow slippage of the liner on the limb, which both damages the skin and degrades comfort and fit. Removal of moisture from space 102 is also important, particularly for the grasp of the socket on the liner. "Suspension" of the socket refers broadly to the maintenance of the socket on the limb; the suspension involves secure maintenance of the socket on the liner, and secure maintenance of the liner on the limb. Further aspects of fluid removal from spaces 101 and 102 and described below, in the context of FIGS. 12-14.

Figure 12:
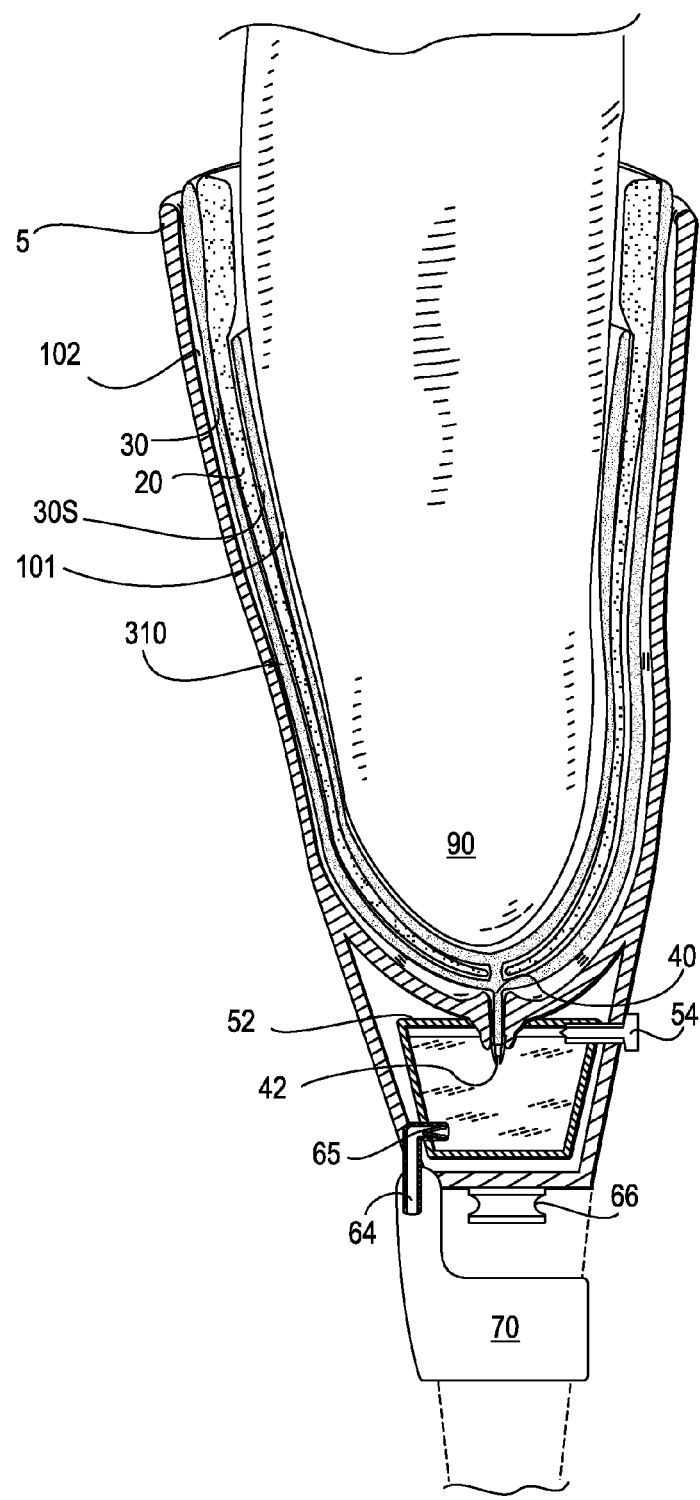
FIG. 12 shows a longitudinal cross sectional view of an embodiment of a prosthetic socket with an embodiment of a prosthetic socket liner disposed therein.

FIG. 12 shows a longitudinal cross sectional view of an embodiment of a prosthetic socket, as represented by socket strut 5, with a liner garment embodiment 310 disposed therein. Liner garment 310 is described above in the context of FIG. 4. Briefly, fluid transport substrate 30 is arranged external to elastomeric portion 20, and fluid transport substrate 30S is arranged in strips internal to elastomeric portion 20. The cross-sectional profile includes the fluid transport strips 30S on both the left and right sides of the image; the intervening spaces between fluid transport strips 30S is not shown; and the pores 22, as shown in FIG. 4 are also not shown. FIG. 12 also shows an interfacing space 101 disposed between the surface of a residual limb 90 and the internal surface of liner 310, and an interfacing space 102 between liner 310 and strut 5 of a prosthetic socket. (These interfacing spaces are also shown in FIGS. 11A-11B.) Distal prosthetic socket structure 50 of prosthetic socket 2 has an annular locking mechanism 52 disposed around distally projecting drain 42 of liner 10. Annular locking mechanism 52 has a lock release mechanism 54, which may be operated either manually and/or automatically. "Annular locking" generally refers to a mechanism that is arranged in ring-like or circumferential manner which locks by an inward or centrally directed force. Distally projecting drain 42 enters reservoir 60, which includes reservoir outlet 64. A distal prosthetic element connecter 66 is disposed at the distal end of distal prosthetic structure 50.

Pump 70 is in fluid connection with reservoir 60. Vacuum, as drawn in reservoir 60 by the action of pump 70, draws fluid from the reservoir, which receives fluid drained both from the fluid transporting or wicking portion 30 of liner 10 as well as from an interfacing space 101 that is disposed between the skin surface of residual limb 90 and liner 10. In one aspect, it may be understood that the fluid transporting portion 30, by virtue of being generally porous, is itself included in the interfacing space between the limb and a substantially impervious elastomeric portion (not shown) of liner 10.

By the pumping action of pump 70 the pressure within reservoir 60 can be dropped to a subatmospheric level. This subatmospheric pressure can be extended into interfacing space 101, inasmuch as that space is in fluid communication with the reservoir. The atmospheric pressure impinging on the external surface of the liner presses the liner against the skin, creating an adherence and resistance to slippage. This effect contributes to a stability of the liner on the skin surface, in effect, a contribution to suspending the liner on the skin. In some embodiments of the technology, the liner is physically connected to the prosthetic socket structure. Thus, the drawing of vacuum by the pump, ultimately contributes to the suspension of the prosthetic socket on the residual limb.

FIGS. 13-14 are diagrams depicting embodiments of methods of transporting fluid, such methods being enabled by embodiments of the moisture management liner as disclosed herein. FIG. 13 is a flow diagram of a method of removing accumulated moisture from within a prosthetic socket fitted with an embodiment of a prosthetic socket liner with moisture management features. In initial steps, a patient dons (step 1301) an embodiment of the moisture management liner in the manner described above. Briefly, donning includes everting the liner garment, contacting it against a distal aspect of the residual limb, and rolling the liner up and around the residual limb, restoring the liner to its normal inside/outside configuration. After donning the liner garment, the patient inserts his or her residual limb into a prosthetic socket (step 1302), makes adjustments to the socket to optimize fit and functionality, and goes about his or her daily activities.

During the course of the day, the residual limb sweats and adds fluid into the space between the residual limb and the liner. Embodiments of the method provide for movement of fluid both distally (step 1303) and radially (step 1305) from that space. Distal movement of moisture may occur through a wicking fabric or substrate 30, as described herein, or by way of channeled structures within a fabric or substrate 32, as described herein. Distal movement is typically by way of capillary action, but may include bulk fluid movement as well. Radial movement refers to movement through a moisture management liner by way of pores 22, as described herein, and may include participation of capillary movement through a wicking substrate as well.

Fluid that moves distally within the fluid transport substrate of the liner, and is eventually moved into the external environment (step 1304). The flow path to the external environment is typically by way of a distal port 40 in the moisture management liner, a distally projecting drain 42, and a reservoir 60. Fluid from the reservoir is ultimately released into the environment, generally by ejection and evaporation. Fluid may also move radially through pores 22 in the liner (step 1306), and thence eventually into the external environment, ultimately by evaporation from an external surface of a moisture management liner embodiment.

FIG. 14 is a flow diagram of a method of removing accumulated moisture from within a prosthetic socket fitted with an embodiment of a prosthetic socket liner with moisture management features. This diagram includes the steps shown in FIG. 13, but the scope of the method is larger in that it also includes management of moisture that may accumulate external to prosthetic socket liner, but within the confines of a prosthetic socket. The focus is on fluid flow paths from two potential sites of fluid accumulation. A first site of fluid accumulation is within a space between the skin of the residual limb and the liner (space 101 in FIG. 12), and second site is a space between the liner and the prosthetic socket structure (space 102 in FIG. 12). The method steps depicted in FIG. 14 occur after the liner garment has been donned and the patient has inserted his or her residual limb in a prosthetic socket (steps 1301 and 1302, as depicted in FIG. 13).

The term "fluid" may refer to any of moisture in liquid form as water, moisture as water vapor, or air. Typically, the fluid in space 101 (between the residual limb and the liner garment) is water in liquid form, although some portion of it may be in vapor form. Generally air from the ambient environment is excluded from the space by the sealing contact between the gel portion of the liner garment at its proximal end and the skin surface of the residual limb, however it may accumulate nevertheless. With these various considerations noted, fluid within space 101 can be moved radially (step 1401) or distally (step 1403). Fluid moved radially (step 1401) is then moved (step 1202) into an environment external to the liner garment, as described above in context of FIG. 13.

Depending on the structure of the prosthetic socket in which the liner garment is disposed and the relative position of the liner within the socket, fluid passing radially (Step 1401) from space 101 can move directly into the external environment (step 1402), or, alternatively it could still be trapped internally within the socket, and therefore contribute to fluid in space 102. The line that connects step 1401 to fluid space 102 represents a pathway that follows from this alternative eventuality. Once the fluid is in space 102, it can move distally, as shown, by way of steps 1404, 1405, and 1406.

Fluid from both spaces 101 (between the skin and the liner garment) and 102 (between the liner garment and the socket) can move distally (independently). Fluid moving distally from space 101 (step 1403) and distally from space 102 (step 1404) converges into a common pool, and moves into a reservoir (step 1405). From the reservoir, fluid is released into the external environment (step 1406).

Any one or more features of any embodiment of the invention, device or method, can be combined with any one or more other features of any other embodiment of the invention, without departing from the scope of the invention.

It should also be understood that the invention is not limited to the embodiments that are described or depicted herein for purposes of exemplification, but is to be defined only by a fair reading of claims appended to the patent application, including the full range of equivalency to which each element thereof is entitled. Further, while some theoretical considerations have been offered to provide an understanding of the technology (as understood by the inventors) such as, for example, the manner in which moisture flows through fluid transport substrates, the claims to the invention are not bound by such theory.

What is claimed is:

1. A moisture management liner device for a prosthetic socket, configured to provide distal movement and radial escape of moisture from the prosthetic socket, the liner device comprising:
    an elongate, cup-shaped, elastomeric member, comprising an elastomeric material and extending from an open proximal end to a substantially closed distal end;
    a fluid exit aperture at the distal end of the elastomeric member, configured to allow fluid to pass out of the liner device;
    multiple longitudinally arranged fluid transport strips, comprising a wicking material and disposed at spaced-apart intervals around a circumference of an internal surface of the elastomeric member, over only a distal portion of the elastomeric member, wherein each of the longitudinally arranged fluid transport strips tapers from a large width at its proximal end to a narrow width at its distal end as the fluid transport strips converge centrally and terminate proximal the fluid exit aperture, and wherein the fluid transport strips are configured to facilitate passage of fluid out of the liner device through the fluid exit aperture; and
    multiple radially-directed pores disposed only on a distal-most region of a proximal portion of the elastomeric member, wherein the pores extend from the internal surface to an external surface of the elastomeric member, wherein the pores are arranged in lines around the circumference of the internal surface, and wherein a proximal-most region of the proximal portion of the elastomeric member has no pores, to facilitate forming an airtight seal between the proximal-most region and a residual limb.

2. The device of claim 1, wherein the elastomeric member comprises a contiguous layer.

3. The device of claim 1, further comprising an outer fluid transport substrate disposed over at least a portion of the external surface of the elastomeric member to facilitate passage of fluid out of the liner device through the pores.

4. The device of claim 3, wherein the pores extend through the outer fluid transport substrate.

5. The device of claim 4, further comprising an inner fluid transport substrate disposed over the internal surface of the proximal portion of the elastomeric member.

6. The device of claim 1, wherein the wicking material of the fluid transport strips comprises a wicking fabric.

7. The device of claim 6, wherein the wicking fabric of the fluid transport strips comprises a breathable mesh fabric.

8. The device of claim 1, further comprising at least one of a valve or a pump attached to the liner device to facilitate unidirectional fluid flow out of the fluid exit aperture of the liner device.

9. The device of claim 1, further comprising:
    a distally projecting outlet in fluid communication with the fluid exit aperture; and
    a prosthetic socket support element, comprising a centrally positioned annular locking mechanism clamped around the distally projecting outlet.

10. The device of claim 9, wherein the distally projecting outlet is also in fluid communication with a fluid residing in an interfacing layer between the liner device and a prosthetic socket to which the liner device is attached.

11. The device of claim 9, further comprising a reservoir, comprising:
    an inlet into which the distally projecting outlet of the liner device drains; and
    an outlet, comprising a one-way valve biased toward allowing fluid to escape the reservoir.

12. The device of claim 1, further comprising:
    a reservoir coupled to the liner device to capture fluid from the device and from an interfacing space between the device and the residual limb; and
    a pump in communication with the reservoir and configured to draw fluid from the reservoir.

13. The device of claim 5, wherein the pores extend through the elastomeric member, the outer fluid transport substrate and the inner fluid transport substrate.

* * * * *